(12) United States Patent
Wainman et al.

(10) Patent No.: US 9,434,914 B2
(45) Date of Patent: Sep. 6, 2016

(54) CLEANING COMPOSITIONS INCLUDING FERMENTED FRUIT SOLUTIONS AND ONE OR MORE BUILDERS

(71) Applicant: EQUATOR GLOBAL LIMITED, Tortola (VG)

(72) Inventors: Peter Nelson Wainman, Bangkok (TH); Sirilak Narongtanupone, Bangkok (TH); Sungworn Sangsri

(73) Assignee: EQUATOR GLOBAL LIMITED, Road Town, Tortola (VG)

( * ) Notice: Subject to any disclaimer, the term of this patent is extended or adjusted under 35 U.S.C. 154(b) by 0 days.

(21) Appl. No.: 14/768,719

(22) PCT Filed: Oct. 16, 2013

(86) PCT No.: PCT/IB2013/002320
§ 371 (c)(1),
(2) Date: Aug. 18, 2015

(87) PCT Pub. No.: WO2015/040445
PCT Pub. Date: Mar. 26, 2015

(65) Prior Publication Data
US 2016/0010037 A1    Jan. 14, 2016

(30) Foreign Application Priority Data

Sep. 20, 2013  (WO) .................. PCT/IB2013/002069
Oct. 2, 2013   (WO) .................. PCT/IB2013/002180

(51) Int. Cl.
*C11D 3/382* (2006.01)
*C11D 3/43* (2006.01)
*C11D 7/44* (2006.01)
*C11D 7/50* (2006.01)
*C11D 3/38* (2006.01)
*C11D 3/00* (2006.01)
*C11D 3/20* (2006.01)
*C11D 3/04* (2006.01)
*C11D 3/22* (2006.01)
*C11D 1/12* (2006.01)
*C11D 1/66* (2006.01)
*C11D 1/90* (2006.01)
*C11D 3/10* (2006.01)

(52) U.S. Cl.
CPC .................. *C11D 3/382* (2013.01); *C11D 1/12* (2013.01); *C11D 1/662* (2013.01); *C11D 1/90* (2013.01); *C11D 3/001* (2013.01); *C11D 3/0047* (2013.01); *C11D 3/0084* (2013.01); *C11D 3/042* (2013.01); *C11D 3/046* (2013.01); *C11D 3/10* (2013.01); *C11D 3/2048* (2013.01); *C11D 3/2079* (2013.01); *C11D 3/2086* (2013.01); *C11D 3/2096* (2013.01); *C11D 3/221* (2013.01); *C11D 3/38* (2013.01)

(58) Field of Classification Search
CPC ........... C11D 3/382; C11D 3/43; C11D 7/44; C11D 7/50; C11D 11/0017; C11D 9/265; C11D 3/042
See application file for complete search history.

(56) References Cited

U.S. PATENT DOCUMENTS

| | | | |
|---|---|---|---|
| 6,653,272 B1 * | 11/2003 | Uyama .............. | C11D 3/38636 435/187 |
| 7,083,727 B2 | 8/2006 | Tanaka et al. | |
| 7,538,079 B2 | 5/2009 | Warr et al. | |
| 2006/0240147 A1 | 10/2006 | Padhye | |
| 2010/0144584 A1 | 6/2010 | Saint Victor | |
| 2010/0233128 A1 | 9/2010 | Panasenko | |
| 2010/0316752 A1 | 12/2010 | Hsu | |
| 2011/0142990 A1 | 6/2011 | Jacob | |
| 2011/0311680 A1 | 12/2011 | Takase et al. | |
| 2012/0246854 A1 | 10/2012 | Uchiyama et al. | |

FOREIGN PATENT DOCUMENTS

| | | |
|---|---|---|
| CN | 101077999 A | 11/2007 |
| CN | 101126052 A | 2/2008 |
| EP | 1178108 A1 | 2/2002 |
| JP | 6219082 A | 1/1987 |
| JP | 2001152188 * | 6/2001 |
| JP | 2001152188 A | 6/2001 |
| JP | 2002003886 A | 1/2002 |
| JP | 2006341236 A | 12/2006 |
| JP | 2010194532 A | 9/2010 |
| WO | 2007049831 A1 | 5/2007 |
| WO | 2012084426 A1 | 6/2012 |

OTHER PUBLICATIONS

Nutrimax Organic "How to Make & Use Garbage Enzyme", 2010, 5 pages.*
Notification of Transmittal of the International Search Report and Written Opinion dated Mar. 18, 2014, in International Application No. PCT/IB2013/02069, 10 pages.
Notification of Transmittal of the International Search Report and Written Opinion dated Dec. 19, 2014, in International Application No. PCT/IB2014/061567, 7 pages.
Notification of Transmittal of the International Search Report and Written Opinion dated Mar. 18, 2014, in International Application No. PCT/IB2013/02180, 9 pages.
Notification of Transmittal of the International Search Report and Written Opinion dated Jul. 30, 2014, in International Application No. PCT/IB2013/02320, 12 pages.

(Continued)

*Primary Examiner* — Charles Boyer
(74) *Attorney, Agent, or Firm* — Rothwell, Figg, Ernst & Manbeck, P.C.

(57) ABSTRACT

Described herein are cleaning compositions comprising fermented fruit solutions and builders, methods for making the same, and methods for using the same. The fermented fruit solutions can contain fruit, sugar and water. The builder can be selected from the group consisting of a non-phosphate builder, such as sodium citrate and sodium bicarbonate, boric acid and mixtures thereof. The cleaning compositions can be used to clean articles, launder articles, clean stains from articles, and clean surfaces.

38 Claims, 5 Drawing Sheets

(56) References Cited

OTHER PUBLICATIONS

Sossou et al. "Study of Pineapple Peelings Processing into Vinegar by Biotechnology" Pakistan Journal of Biological Sciences, vol. 12(11):859-865, 2009.
Jekle "Fruit wine—traditional Thai style" Pibulsongkram Rajabhat University, Department of Argo-Industry, Faculty of Food and Agricultural Technology, Phitsanulok, 2005, 5 pages.
Feijoo-Siota et al. "Native and Biotechnology Engineered Plant Proteases with Industrial Applications" Food Bioprocess Technol., Springer, 2010, 23 pages.
Balandrin et al. "Natural Plant Chemicals: Sources of Industrial and Medicinal Materials" Science, New Series, vol. 228, No. 4704, 1985, American Association for the Advancement of Science, pp. 1154-1160.
Australian Government, Department of Health and Ageing, Office of the Gene Technology Regulator "The Biology of *Ananas comosus* var. *comosus* (Pineapple)", Version 2, 2008, 43 pages.
Martinyz "How to make your own Eco-Enzyme Detergent" 2011, printed from http://martinyz.hubpages.com/hub/How-to-make-your-own-Eco-Enzyme-Detergent, on Sep. 5, 2013, 3 pages.
Lee "Citrus Enzyme Cleaner Recipe" 2012, printed from http://www.ecokaren.com/2012/05/citrus-enzyme-cleaner-recipe/, on Sep. 6, 2013, 4 pages.

* cited by examiner

CLEANING COMPOSITIONS INCLUDING FERMENTED FRUIT SOLUTIONS AND ONE OR MORE BUILDERS

CROSS REFERENCE TO RELATED APPLICATION(S)

This application is a 35 U.S.C. §371 National Phase Entry Application from PCT/IB2013/002320, filed Oct. 16, 2013, designating the United States, which also claims the benefit of International Application No. PCT/IB2013/002069, filed Sep. 20, 2013 and International Application No. PCT/IB2013/002180, filed Oct. 2, 2013. The disclosures of all applications are incorporated herein in their entirety by reference.

TECHNICAL FIELD

The present invention relates generally to cleaning compositions and, more particularly, to cleaning compositions comprising fermented fruit solutions, methods for making the same, and methods for using the same.

BACKGROUND

Cleaning products are commonly used in day to day life, whether it be to clean a home, clean clothes, or for industrial purposes. Common cleaning products are used across the world and can include for example, laundry detergents, stain removers, fabric softeners, floor cleaners, bathroom cleaners, dishwashing products, kitchen cleaners, liquid soap, and multi-purpose cleaners. Most common cleaning products use a relatively toxic (to either health and/or to the environment) mix of chemicals as many such products contain certain ingredients derived from petrochemicals. Products derived from petrochemicals may be harmful since either the final mix of ingredients may contain toxic chemicals and/or the manufacture of these products also may result in the production of harmful by-products.

Natural products are an alternative to toxic petroleum based cleaning products. Examples of natural cleaning products include fermented fruit solutions with other natural based components. Natural products, typically however, do not clean as well as their petroleum based counterparts. Specifically, natural products, historically, are not comparable to leading laundry detergent products and leading laundry stain remover products in terms of cleaning ability. Thus, there is a need for natural based cleaning products with superior cleaning capabilities.

SUMMARY

The present invention provides for natural cleaning compositions comprising fermented fruit solutions and builders. The cleaning compositions of the present invention have been shown to be comparable to leading brand name products in terms of cleaning ability after exhaustive testing. Following exhaustive testing, it was determined that the claimed compositions produce products that can be used to launder an article and to clean stains from an article either similar to or better than leading petroleum linked mass market products.

Embodiments of the present invention include cleaning compositions. The cleaning compositions comprise a fermented fruit solution. The fermented fruit solution has a total acid content that is greater than or equal to 3.0%. The fermented fruit solution is prepared by fermenting a pre-fermented fruit solution with lactic acid bacteria. The pre-fermented fruit solution comprises about 2 to about 20 weight percent of a sugar based on the total weight of the pre-fermented fruit solution. The pre-fermented fruit solution further comprises about 20 to about 50 weight percent of a fruit puree based on the total weight of the pre-fermented fruit solution, wherein the fruit puree comprises more than 90% pineapple fruit. The pre-fermented fruit solution further comprises about 30 to about 75 weight percent of a water based on the total weight of the pre-fermented fruit solution. The pH of the pre-fermented fruit solution is about 5.5 to about 9.0. The brix level of the pre-fermented fruit solution is about 12% to about 24%. The cleaning composition also includes one or more builders. The total weight percent of the one or more builders is about 2 to about 30 weight percent based on the total weight of the composition.

Embodiments of the present invention include methods of making cleaning compositions. The method comprises preparing a pre-fermented fruit solution. The pre-fermented fruit solution comprises about 2 to about 20 weight percent of a sugar based on the total weight of the pre-fermented fruit solution. The pre-fermented fruit solution further comprises about 20 to about 50 weight percent of a fruit puree based on the total weight of the pre-fermented fruit solution, wherein the fruit puree comprises more than 90% pineapple fruit. The pre-fermented fruit solution further comprises about 30 to about 75 weight percent of a water based on the total weight of the pre-fermented fruit solution. The pH of the pre-fermented fruit solution is about 5.5 to about 9.0. The brix level of the pre-fermented fruit solution is about 12% to about 24%. The method further comprises fermenting the pre-fermented fruit solution with lactic acid bacteria to create a fermented fruit solution with a total acid content of greater than or equal to 3.0%. The method further comprises mixing the fermented fruit solution with one or more builders, wherein the total weight percent of the one or more builders is about 2 to about 30 weight percent based on the total weight of the composition.

Embodiments of the present invention include methods for cleaning an article with a cleaning composition comprising a fermented fruit solution and one or more builders. Further embodiments of the present invention include methods for laundering an article with the cleaning composition comprising a fermented fruit solution and one or more builders. Further embodiments of the present invention include methods for cleaning a stain from an article with a cleaning composition comprising a fermented fruit solution and one or more builders. Further embodiments of the present invention include methods for cleaning surfaces, such as floors, countertops or other types of surfaces, with a cleaning composition comprising a fermented fruit solution and one or more builders.

BRIEF DESCRIPTION OF THE FIGURES

The accompanying drawings, which are incorporated herein and form part of the specification, illustrate various embodiments of the present disclosure and, together with the description, further serve to explain the principles of the disclosure and to enable a person skilled in the pertinent art to make and use the embodiments disclosed herein.

DETAILED DESCRIPTION

Figure 1:
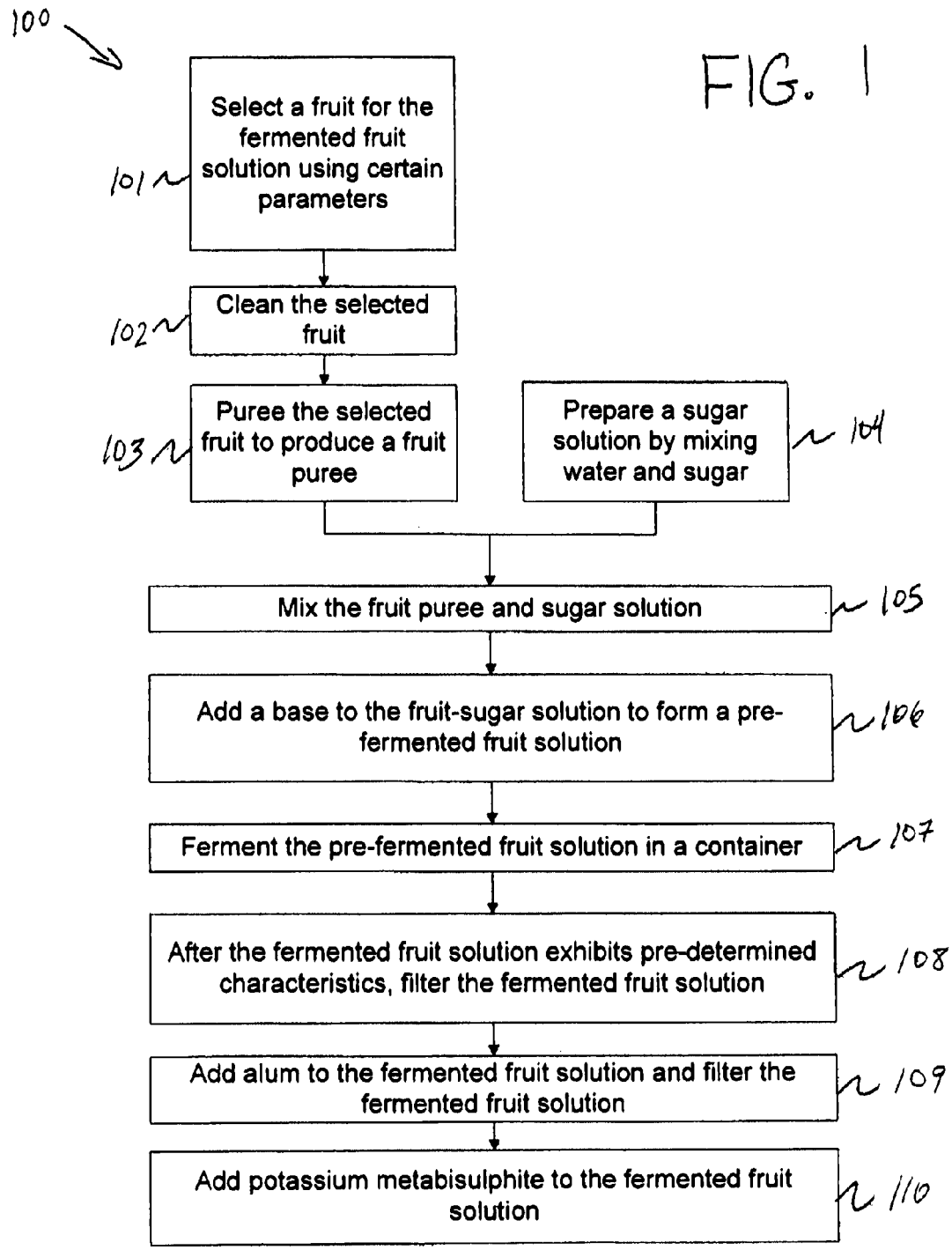
FIG. 1 illustrates a flow diagram of an exemplary method of making fermented fruit solutions in accordance with exemplary embodiments of the present invention.

The present invention relates generally to natural cleaning compositions comprising fermented fruit solutions, methods for making the same, and methods for using the same. The fermented fruit solutions can contain fruit, sugar and water. As defined herein, cleaning compositions include, but are not limited to, laundry detergents, stain removers, fabric softeners, surface cleaners (including but not limited to floor cleaners and countertop cleaners), bathroom cleaners, dishwashing products, kitchen cleaners, liquid soap, multi-purpose cleaners and the like.

Embodiments of the present invention include fermented fruit solutions for use with cleaning compositions. The fermented fruit solutions can include a pre-fermented fruit solution that is fermented with lactic acid bacteria. The pre-fermented fruit solution is prepared prior to fermentation and may comprise fruit puree, sugar and water in various amounts.

The fruit puree can be a mashed up fruit mixture comprising predominately pineapple. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple. The portion of the fruit mixture that does not comprise pineapple can comprise other fruits such as lime. Any or some or all parts of the pineapple can be used, provided that more than just the crown of the pineapple is used. Preferably, the entirety of the pineapple including the crust/shell minus the crown of the pineapple can be used. Preferably, the brix level of the fruit is greater than or equal to 10%. Even more preferably, the brix level is greater than or equal to 12%.

The pre-fermented fruit solution can comprise fruit puree in amounts from about 20 to about 50 weight percent based on the total weight of pre-fermented fruit solution. More preferably, the pre-fermented fruit solution can comprise fruit puree in amounts from about 35 to about 40 weight percent based on the total weight of pre-fermented fruit solution. Most preferred, the pre-fermented fruit solution comprises 37.5 weight percent of fruit puree based on the total weight of the pre-fermented fruit solution.

The pre-fermented fruit solution also contains a sugar. The sugar can be any sugar including a type of disaccharide, oligosaccharide and/or a type of monosaccharide. The sugar can be in either solid or liquid form. Preferably, the sugar is sucrose. The pre-fermented fruit solution can comprise sugar in amounts from about 2 to about 20 weight percent based on the total weight of pre-fermented fruit solution. More preferably, the pre-fermented fruit solution can comprise sugar in amounts from about 10 to about 15 weight percent based on the total weight of the pre-fermented fruit solution. Even more preferably, the pre-fermented fruit solution can comprise sugar in an amount of about 12.5 weight percent based on the total weight of the pre-fermented fruit solution.

The pre-fermented fruit solution can also comprise water. The pre-fermented fruit solution can comprise water in amounts from about 30 to about 75 weight percent based on the total weight of the pre-fermented fruit solution. The pre-fermented fruit solution can comprise water in amounts from about 40 to about 60 weight percent based on the total weight of pre-fermented fruit solution. More preferably, the pre-fermented fruit solution can comprise water in an amount of about 50 weight percent based on the total weight of the pre-fermented fruit solution.

The brix level of the pre-fermented solution can be between about 12% to about 24%. Additionally, a base can be added to the pre-fermented solution to adjust the pH of the solution. Examples of bases for use with the present invention include sodium hydroxide, potassium hydroxide and alkyl poly glucoside ("APG"). Preferably the pH is adjusted to a pH between 5.5 and 9.0. More preferably, the pH is adjusted to a pH of 6.0 to 8.0.

The pre-fermented solution is fermented with lactic acid bacteria until the total acid content and total sugar content reach preferred levels. The pre-fermented solution can be fermented with lactic acid bacteria naturally produced from the selected fruit. Alternatively or additionally, a lactic acid bacteria starter can be added to the pre-fermented solution. Preferably, the pre-fermented solution is fermented until the total acid content is greater than or equal to 2%, 3% or 4%. More preferably, the pre-fermented solution is fermented until the total acid content is greater than or equal to 5%. The total acid content can be measured using a titration method. Preferably, the pre-fermented solution is fermented until the total sugar content is less than or equal to 0.10%. More preferably, the pre-fermented solution is fermented until the total sugar content is less than or equal to 0.05%. The total sugar content can be measured using a dinitrosalicylic colorimetric ("DNS") method. Once such parameters of total sugar and total acid are met, we refer to this solution below as the fermented solution.

The fermented solution is then filtered. After filtering, alum can be added to the fermented solution to aid with the filtration of sediment from the solution. Alum can be added in an amount ranging from 0.5 to 1.0 weight percent based on the total weight of the solution. After greater than or equal to 24 hours, the sediment can be removed from the solution after the addition of alum.

Potassium metabisulphite can be added to the fermented solution to stop the fermentation process. Potassium metabisulphite can be added in an amount from about 0.001 to about 0.2 weight percent based on the total weight of the fermented fruit solution. Preferably, potassium metabisulphite can be added in an amount from about 0.01 to about 0.1 weight percent based on the total weight of the fermented fruit solution.

Embodiments of the present invention also include methods of making fermented fruit solutions for use with cleaning compositions.

Referring now to FIG. 1, a flow diagram illustrating the steps of a method of making fermented fruit solutions in accordance with exemplary embodiments of the present invention is provided. In an embodiment of the present invention, method 100 includes selecting one fruit (step 101). The fruit used is predominately pineapple. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple. The remaining percentage of the fruit puree can comprise an additional fruit such as lime. Any or some or all parts of the pineapple can be used, provide that more than just the crown of the pineapple is used. Preferably, the entirety of the pineapple including the crust/shell minus the crown of the pineapple can be used.

In selecting the fruit to puree, it is preferable that the brix level of the fruit is greater than or equal to 10%. Even more preferably, the brix level must be greater than or equal to 12%. The brix level of the fruit can be determined by measuring the brix level of the fruit puree using a refractometer.

Next, in method 100, the selected fruit can be cleaned (step 102). The fruit can be cleaned by soaking the fruit in water with already created fermented fruit solution. As the final fermented fruit solution is a cleaning solution, the fermented fruit solution can be used to effectively clean the fruit for future production. The fermented fruit solution is a natural surfactant that helps clean pesticides and other impurities within the fruit. Additionally, the fermented fruit solution contains lactic acid bacteria, to aid with the fermentation of the pre-fermented fruit solution.

The weight percent of the fermented fruit solution used for cleaning the fruit can be greater than or equal to 5% fermented fruit solution, with the remaining amount comprising water. The total acid content of the fermented fruit solution can be greater than or equal to 3%. The fruit can be soaked in the fermented fruit solution for greater than or equal to three hours.

Alternatively, but less preferably, the fruit can be cleaned with only water. The fruit can be soaked in the solution of water for greater than or equal to 24 hours.

Next, the method of making fermented fruit solutions can include pureeing a fruit to produce a fruit puree (step 103). The fruit puree can be obtained by grinding the fruit into a puree. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple.

As illustrated in FIG. 1, the method of making fermented fruit solutions can include preparing a sugar solution by mixing water and sugar (step 104). The sugar solution can be prepared by mixing about 3 to about 40 weight percent of a sugar with about 60 to about 97 weight percent of a water to form a sugar solution. Preferably, the sugar solution can be prepared by mixing about 14 to about 27 weight percent of a sugar with about 73 to about 86 weight percent of a water. More preferably, the sugar solution can be prepared by mixing about 20 weight percent of a sugar with about 80 weight percent of a water. The sugar and water can be mixed with an electric stirrer. The sugar can be any sugar including a type of disaccharide, oligosaccharide and/or a type of monosaccharide. The sugar can be in either solid or liquid form. Preferably, the sugar is sucrose. The brix level of the sugar solution preferably is greater than or equal to 19%. The brix level of the sugar solution can be determined by using a refractometer.

As illustrated in FIG. 1, the method of making fermented fruit solutions can include mixing the fruit puree and sugar solution (step 105). The mixture can be prepared by mixing about 20 to about 50 weight percent of the fruit puree with about 50 to about 80 weight percent of the sugar solution to produce a fruit-sugar solution, wherein the weight percents are based on the total weight of the fruit-sugar solution. Preferably, the mixture can be prepared by mixing about 35 to about 38 weight percent of the fruit puree with about 62 to about 65 weight percent of the sugar solution. More preferably, the mixture can be prepared by mixing about 37.5 weight percent of the fruit puree with about 62.5 weight percent of the sugar solution. The fruit puree and sugar solution can be mixed with an electric stirrer.

As illustrated in FIG. 1, the method of making fermented fruit solutions can include adding a base to the fruit-sugar solution to form a pre-fermented fruit solution (step 106). A base can be added to the fruit-sugar solution such that it produces a pre-fermented fruit solution with a pH of about 5.5 to about 9.0. Preferably, a base can be added to the fruit-sugar solution such that it produces a pre-fermented fruit solution with a pH of about 6.0 to about 8.0. The base can be selected from the group consisting of sodium hydroxide, potassium hydroxide and APG. After addition of the base, the pre-fermented fruit solution preferably has a brix level of about 12% to about 24%. More preferably, the pre-fermented fruit solution has a brix level of about 15% to about 24%. The brix level of the pre-fermented fruit solution can be determined by using a refractometer.

As illustrated in FIG. 1, the method of making fermented fruit solutions can include fermenting the pre-fermented fruit solution in a closed container (step 107). In certain embodiments of the invention, the pre-fermented fruit solution can fill the container in an amount between about 85% to about 90%. In certain embodiments of the invention, the container is a 200 liter polyethylene plastic tank with a lid. The remainder of the container can be air. The container can be secured with a clamp device to ensure that the pre-fermented fruit solution is not exposed to outside environmental conditions or contaminants. The container can be stored at ambient temperature in tropical climates, for instance at temperatures ranging from 27 to 45° C.

The pre-fermented fruit solution can be allowed to ferment until the solution exhibits certain characteristics. The characteristics that can be observed to aid in the determination of when to stop fermentation can include the total sugar content, total acid content, electrical conductivity, total microbial count, lactic acid bacteria count, and/or yeast and mold count. The characteristics of the pre-fermented fruit solution can be observed at set intervals. The characteristics can be observed on a weekly or monthly basis.

The pre-fermented fruit solution can be fermented until it exhibits a total sugar content that is close to or equal to zero percent. Preferably, the pre-fermented fruit solution is allowed to ferment until the total sugar content is less than or equal to 0.10%. More preferably, the pre-fermented solution is allowed to ferment until the total sugar content is less than or equal to 0.05%.

The pre-fermented fruit solution can be fermented until it exhibits a total acid content that reaches a certain level. Preferably, the pre-fermented fruit solution is allowed to ferment until the total acid content is greater than or equal to 2%, 3% or 4%. More preferably, the pre-fermented solution is allowed to ferment until the total acid content is greater than or equal to 5%.

As illustrated in FIG. 1, after the solution exhibits certain pre-determined characteristics, the fermented fruit solution can be filtered (step 108). The fermented fruit solution can be filtered with a filter to separate crusts. An example of a filter for use with the present invention is a cloth filter.

Following filtration, alum can be added to the fermented fruit solution and the fermented fruit solution can once again be filtered (step 109). Alum can be added to the fermented fruit solution to aid with the settling of sediment. Alum can be added in an amount ranging from about 0.5 weight percent to 1.0 weight percent based on the total weight of the fermented fruit solution. After addition of alum, the fermented fruit solution can sit for greater than or equal to 24 hours. The fermented fruit solution can then be filtered. The fermented fruit solution can be filtered using a filter. An example of a filter for use with the present invention is a cloth filter.

As illustrated in FIG. 1, the method of making fermented fruit solutions can include adding potassium metabisulphite to the fermented fruit solution (step 110). Potassium metabisulphite can be added to the fermented fruit solution once the solution exhibits certain characteristics, as described above. Potassium metabisulphite can be added to stop the fermentation process. Potassium metabisulphite can be added in an amount from about 0.001 to about 0.2 weight percent based on the total weight of the fermented fruit solution. Preferably, potassium metabisulphite can be added in an amount from about 0.01 to about 0.1 weight percent based on the total weight of the fermented fruit solution. After adding potassium metabisulphite, the fermented fruit solution should be allowed to sit for a minimum of 3 hours.

Following the addition of potassium metabisulphite, the fermented fruit solution can be used in a cleaning composition. The fermented fruit solution can be used in cleaning compositions, including for example laundry detergents, stain removers, fabric softeners, floor cleaners, bathroom cleaners, dishwashing products, kitchen cleaners, liquid soap, and multi-purpose cleaners.

Figure 2:
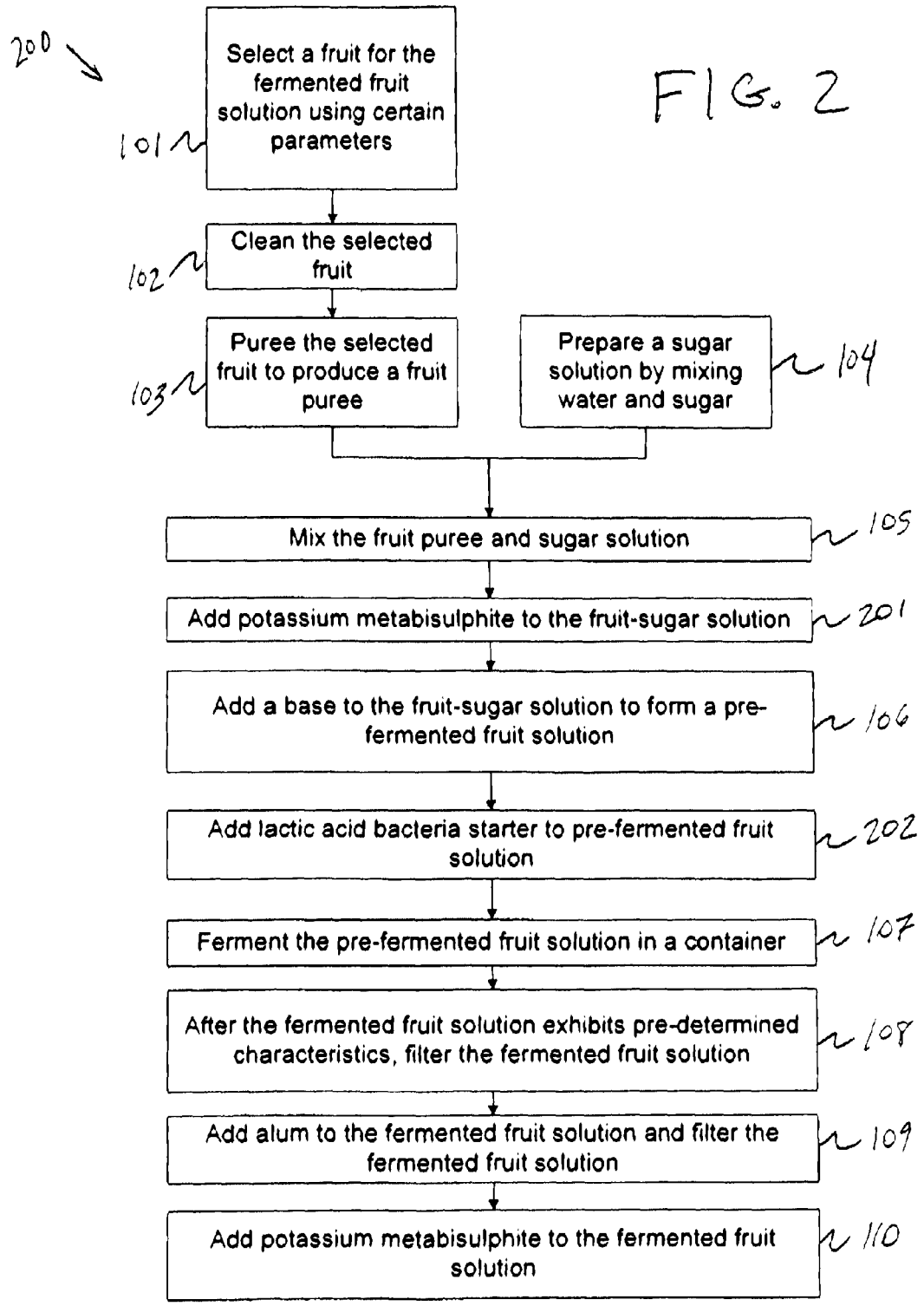
FIG. 2 illustrates a flow diagram of a second exemplary method of making fermented fruit solutions in accordance with exemplary embodiments of the present invention.

Referring now to FIG. 2, a flow diagram illustrating the steps of a method of making fermented fruit solutions in accordance with exemplary embodiments of the present invention is provided. In an embodiment of the present invention, method 200 includes several of the same steps described above in reference to method 100.

In method 200, the selected fruit can be cleaned (step 102). The fruit can be cleaned by soaking the fruit in water with already created fermented fruit solution. As the final fermented fruit solution is a cleaning solution, the fermented fruit solution can be used to effectively clean the fruit for future production. The fermented fruit solution is a natural surfactant that helps clean pesticides and other impurities within the fruit.

The weight percent of the fermented fruit solution used for cleaning the fruit can be greater than or equal to 5% fermented fruit solution, with the remaining amount comprising water. The total acid content of the fermented fruit solution can be greater than or equal to 3%. The fruit can be soaked in the fermented fruit solution for greater than or equal to three hours.

Alternatively, but less preferably, the fruit can be cleaned with only water. The fruit can be soaked in the solution of water for greater than or equal to 24 hours.

The fruit can then be pureed to produce a fruit puree. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple.

As illustrated in FIG. 2, method 200 can include adding potassium metabisulphite to the fruit-sugar solution after the fruit sugar solution is prepared by mixing the fruit puree and sugar solution (step 201). Potassium metabisulphite can be used to kill all micro-organisms in the fruit-sugar solution including yeast and mold. After adding potassium metabisulphite and adjusting pH of the fruit-sugar solution (see step 106), lactic acid bacteria can be added.

As illustrated in FIG. 2, method 200 can include adding lactic acid bacteria starter to the pre-fermented fruit solution (step 202). The lactic acid bacteria starter can be added to the pre-fermented fruit solution to help with fermentation of the pre-fermented fruit solution.

Embodiments of the present invention also include methods of cleaning an article with a cleaning composition comprising a fermented fruit solution. Following preparation of the fermented fruit solutions described above, the fermented fruit solutions can be used to clean an article. Methods of the invention can comprise using a cleaning composition with a fermented fruit solution to launder an article. Methods of the invention can also comprise using a cleaning composition with a fermented fruit solution to remove a stain from an article. Methods of the invention can also comprise using a cleaning composition with a fermented fruit solution to clean and soften an article. Methods of the invention can also comprise using a cleaning composition with a fermented fruit solution to clean any type of surface, including but not limited to floors, bathrooms, dishes, tabletops, windows, and kitchens. Methods of the invention can also comprise using a cleaning composition with a fermented fruit solution to wash hands or a body (either human or otherwise), as a liquid soap product.

Embodiments of the present invention include cleaning compositions comprising fermented fruit solutions and builders. The cleaning compositions can include a fermented fruit solution such as the above described fermented fruit solutions. The cleaning compositions can be used as laundry detergents, stain removers and surface cleaners.

The cleaning compositions can include one or more builders. In preferred embodiments of the present invention, the one or more builders is selected from the group consisting of a non-phosphate builder, boric acid and mixtures thereof. Examples of non-phosphate builders for use with the present invention include, but are not limited to, sodium citrate and sodium bicarbonate. Preferably, the total weight percent of the one or more builders is about 2 to about 30 weight percent based on the total weight of the composition. More preferably, the total weight percent of the one or more builders is about 5 to about 30 weight percent. More preferably, the total weight percent of the builder is about 10 to about 28 weight percent. Even more preferably the total weight percent of the one or more builders is about 15 to about 27.5 weight percent.

In certain embodiments of the present invention, the one or more builders is a mixture of sodium citrate and boric acid. In embodiments where the cleaning composition comprises a mixture of sodium citrate and boric acid, sodium citrate can be present in amount of about 5 to about 25 weight percent based on the total weight of the composition, and boric acid can be present in an amount of about 0.5 to about 5 weight percent based on the total weight of the composition. More preferably, in embodiments where the cleaning composition comprises a mixture of sodium citrate and boric acid, sodium citrate can be present in amount of about 15 to about 25 weight percent based on the total weight of the composition, and boric acid can be present in an amount of about 1 to about 3 weight percent based on the total weight of the composition. Even more preferably, in embodiments where the cleaning composition comprises a mixture of sodium citrate and boric acid, sodium citrate can be present in amount of about 20 to about 25 weight percent based on the total weight of the composition, and boric acid can be present in an amount of about 1.5 to about 2.5 weight percent based on the total weight of the composition.

In certain embodiments of the present invention, the one or more builders is sodium citrate. In embodiments where the builder is sodium citrate, the builder can be present in a range of about 5 weight percent to about 25 weight percent based on the total weight of the composition. In embodiments where the builder is sodium citrate, the builder can be present in a range of about 10 weight percent to about 25 weight percent. Even more preferably, in embodiments where the builder is sodium citrate, the builder can be present in a range of about 15 weight percent to about 21 weight percent. In other preferred embodiments where the builder is sodium citrate, the builder can be present in an amount of about 16 weight percent to about 19 weight percent.

The cleaning compositions can include at least one natural based surfactant. Natural based surfactants include but are not limited to sodium lauryl sulfate (plant-based version), cocamidopropyl betaine, and alkyl polyglycoside. Preferably, the cleaning composition can include at least one surfactant selected from the group consisting of sodium lauryl sulfate, cocamidopropyl betaine, alkyl polyglycoside and mixtures thereof. Further, the cleaning composition can comprise at least one surfactant in an amount of about 1 to about 23 weight percent based on the total weight of the composition. Preferably, the at least one surfactant is present in an amount of about 1 to about 15 weight percent based on the total weight of the composition. More preferably, the at least one surfactant is present in an amount of about 2 to about 15 weight percent based on the total weight of the composition. Even more preferably, the at least one surfactant is present in an amount of about 5 to about 15 weight percent based on the total weight of the composition.

In certain preferred embodiments of the present invention, the at least one surfactant is sodium lauryl sulfate. In certain embodiments of the present invention where the surfactant is sodium lauryl sulfate, sodium lauryl sulfate is preferably present in an amount of about 1 to about 15 weight percent based on the total weight of the composition. More preferably, in certain embodiments of the present invention where the surfactant is sodium lauryl sulfate, sodium lauryl sulfate is present in an amount of about 5 to about 15 weight percent based on the total weight of the composition. Even more preferably, in certain embodiments of the present invention where the surfactant is sodium lauryl sulfate, sodium lauryl sulfate is present in an amount of about 8 to about 15 weight percent based on the total weight of the composition.

In other preferred embodiments of the present invention, the at least one natural based surfactant is alkyl polyglycoside. Preferably, in certain embodiments of the present invention where the surfactant is alkyl polyglycoside, alkyl polyglycoside is present in an amount of about 1 to about 15 weight percent based on the total weight of the composition. More preferably, in certain embodiments of the present invention where the surfactant is alkyl polyglycoside, alkyl polyglycoside is present in an amount of about 2 to about 8 weight percent based on the total weight of the composition. Even more preferably, in certain embodiments of the present invention where the surfactant is alkyl polyglycoside, alkyl polyglycoside is present in an amount of about 5 to about 6.5 weight percent based on the total weight of the composition.

The cleaning compositions can include at least one thickener. In preferred embodiments of the invention, the thickener is at least one selected from the group consisting of natural gums, sodium chloride and mixtures thereof. Examples of natural gums that can be used with the present invention include guar gum, xantham gum, and gum arabic. Preferably, the thickener is present in an amount of about 0.1 to about 2 weight percent based on the total weight of the composition.

The cleaning compositions can include at least one emulsifier. In preferred embodiments of the present invention, the at least one emulsifier is glycerol. Preferably, the at least one emulsifier is present in an amount of about 0.1 to about 2.5 weight percent based on the total weight percent of the composition.

The cleaning compositions can include at least one solvent, wherein the solvent is not water. In preferred embodiments of the invention, the at least one solvent is ethanol. Preferably, the solvent is present in an amount of about 0.2 to about 2 weight percent based on the total weight of the composition. More preferably, the solvent is present in an amount of about 0.5 to about 2 weight percent based on the total weight of the composition.

The cleaning compositions can include at least one anti-foam agent or foam stabilizer. In preferred embodiments, the anti-foam agent can be oleic acid, lactic acid or mixtures thereof. Preferably, the at least one anti-foam agent is present in an amount of about 0.3 to about 2 weight percent based on the total weight of the composition.

The cleaning compositions can include at least one corrosion inhibitor. In preferred embodiments of the present invention, the at least one corrosion inhibitor is selected from the group consisting of gum arabic, sodium polyaspartate and mixtures thereof. Preferably, the at least one corrosion inhibitor is present in an amount of about 0.1 to about 2.5 weight percent based on the total weight of the composition.

The cleaning compositions can include at least one pH adjusting agent. In preferred embodiments of the present invention, the at least one pH adjusting agent is selected from the group consisting of sodium hydroxide, potassium hydroxide and mixtures thereof. Preferably, the at least one pH adjusting agent is present in an amount of about 0.01 to about 2 weight percent based on the total weight of the composition.

The cleaning compositions can also include a preservative and/or an essential oil. Examples of preservatives for use with the present invention include benzoic acid, potassium sorbate, nisin, natamycin, and mixtures thereof. Preferably, the preservative is selected from the group consisting of potassium sorbate, nisin, natamycin, and mixtures thereof. Additionally, boric acid, which is suitable for use as a builder in the present invention, can also be used as a preservative in the present invention. The preservative, in addition to boric acid, can be present in an amount of not greater than about 1 weight percent based on the total weight of the composition.

The cleaning compositions can also include water. The remainder of the weight percent can be water.

Figure 3:
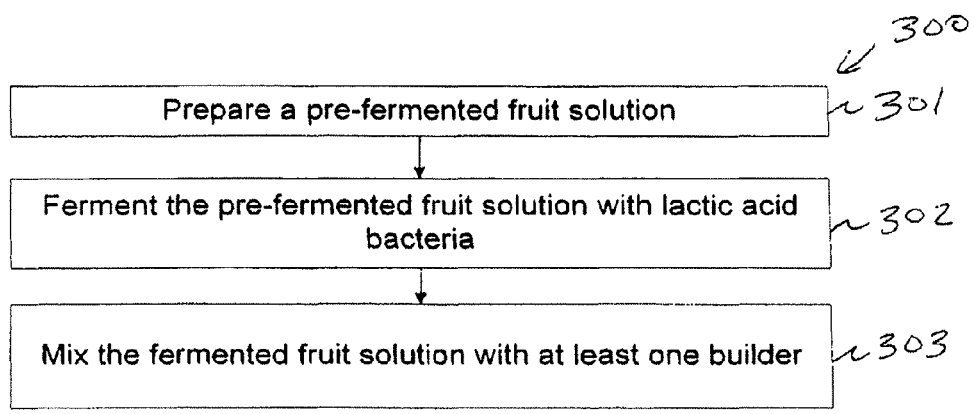
FIG. 3 illustrates a flow diagram of an exemplary method of making cleaning compositions in accordance with exemplary embodiments of the present invention.

Embodiments of the present invention include methods of making cleaning compositions. Referring now to FIG. 3, a flow diagram illustrating the steps of a method of making cleaning compositions in accordance with exemplary embodiments of the present invention is provided. In an embodiment of the present invention, method 300 includes preparing a pre-fermented fruit solution (step 301). The pre-fermented fruit solution can be prepared in accordance with the above described methods, for example methods 100 and 200. As described in detail above, the pre-fermented fruit solution is prepared prior to fermentation and may comprise fruit puree, sugar and water in various amounts.

Next, in method 300, the pre-fermented fruit solution can be fermented with lactic acid bacteria to create a fermented fruit solution (step 302). The pre-fermented fruit solution can be fermented as described in detail above, for example in methods 100 and 200.

Next, in method 300, the fermented fruit solution can be mixed with one or more builders (step 303). The total weight percent of the one or more builders can be about 2 to about 30 weight percent based on the total weight of the composition. In certain embodiments of the claimed invention, the mixing can be performed at temperatures between 25° C. to 35° C. A high speed mixer or homogenizer can be used to perform the mixing. In preferred embodiments of the present invention, the one or more builders is selected from the group consisting of a non-phosphate builder, boric acid and mixtures thereof. Examples of non-phosphate builders for use with the present invention include, but are not limited to, sodium citrate and sodium bicarbonate. In certain embodiments of the present invention, the builder is a mixture of sodium citrate and boric acid. Preferably, the total weight percent of the one or more builders is about 2 to about 30 weight percent based on the total weight of the composition. More preferably, the builder is used in an amount of about 5 to about 30 weight percent. Even more preferably, the builder is used in an amount of about 10 to about 28 weight percent. Most preferably, the builder is used in an amount of about 15 to about 27.5 weight percent.

In certain embodiments of the present invention, the one or more builders is a mixture of sodium citrate and boric acid. In embodiments where the cleaning composition comprises a mixture of sodium citrate and boric acid, sodium citrate can be used in amount of about 5 to about 25 weight percent based on the total weight of the composition, and boric acid can be used in an amount of about 0.5 to about 5 weight percent based on the total weight of the composition. More preferably, in embodiments where the cleaning composition comprises a mixture of sodium citrate and boric acid, sodium citrate can be used in amount of about 15 to about 25 weight percent based on the total weight of the composition, and boric acid can be used in an amount of about 1.0 to about 3 weight percent based on the total weight of the composition. Even more preferably, in embodiments where the cleaning composition comprises a mixture of sodium citrate and boric acid, sodium citrate can be used in amount of about 20 to about 25 weight percent based on the total weight of the composition, and boric acid can be used in an amount of about 1.5 to about 2.5 weight percent based on the total weight of the composition.

In certain embodiments of the present invention, the builder is sodium citrate. In embodiments where the builder is sodium citrate, the sodium citrate can be used in amount of about 5 weight percent to about 25 weight percent based on the total weight of the composition. More preferably, in embodiments where the builder is sodium citrate, the sodium citrate can be used in amount of about 10 to about 25 weight percent based on the total weight of the composition. Even more preferably, in embodiments where the builder is sodium citrate, the sodium citrate can be used in an amount of about 15 to about 21 weight percent based on the total weight of the composition. In other preferred embodiments where the builder is sodium citrate, the builder can be used in an amount of about 16 weight percent to about 19 weight percent.

Figure 4:
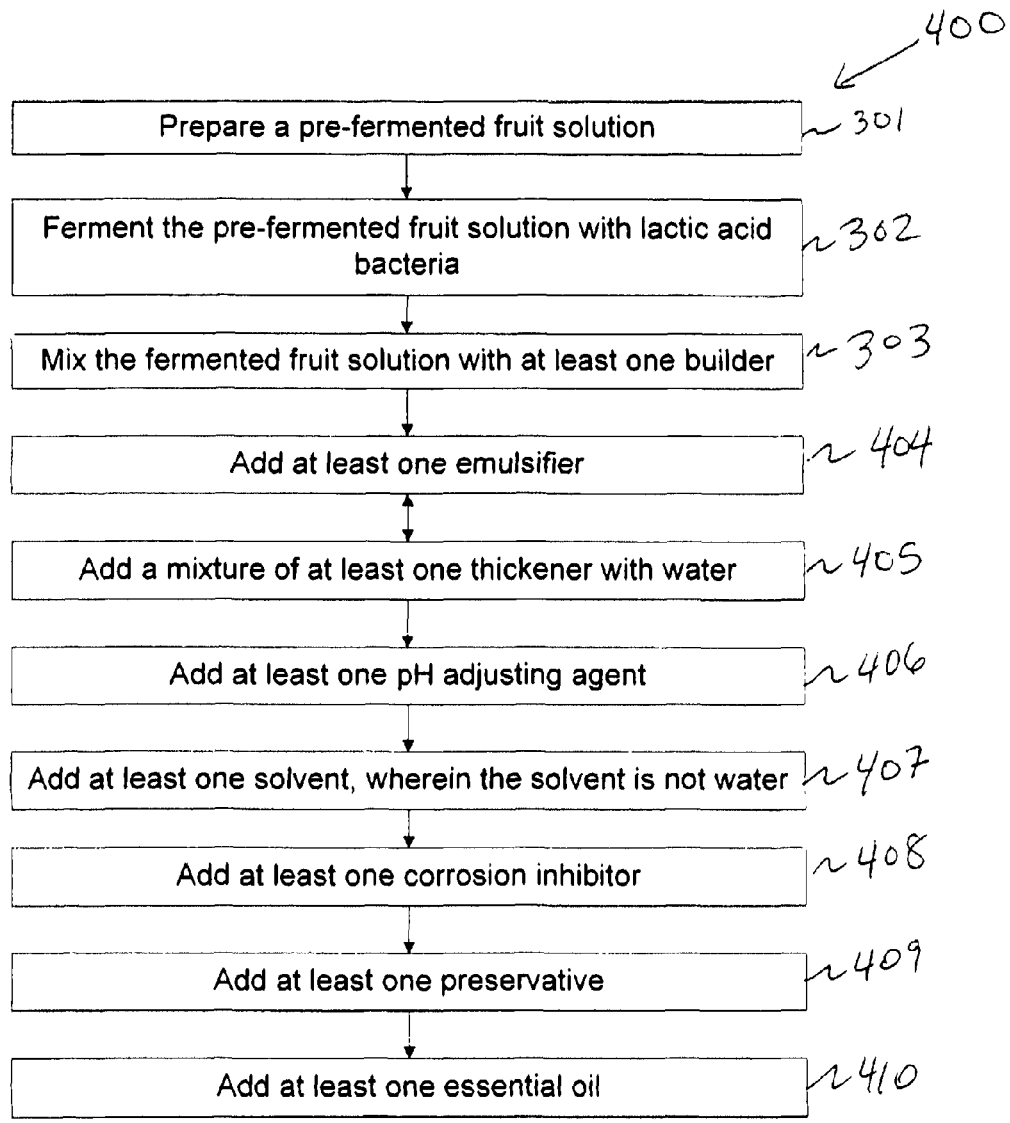
FIG. 4 a flow diagram of a second exemplary method of making cleaning compositions in accordance with exemplary embodiments of the present invention.

Referring now to FIG. 4, a flow diagram illustrating the steps of a method of making cleaning compositions in accordance with exemplary embodiments of the present invention is provided. In an embodiment of the present invention, method 400 includes several of the same steps of method 300, including steps 301, 302, and 303.

Next, in method 400, at least one emulsifier can be added to the mixture (step 404). In preferred embodiments of the present invention, the at least one emulsifier is glycerol. Preferably, the at least one emulsifier is used in an amount of about 0.1 to about 2.5 weight percent based on the total weight percent of the composition.

Method 400 can further include adding a mixture of at least one thickener with water (step 405). In preferred embodiments of the invention, the thickener is at least one selected from the group consisting of natural gums, sodium chloride and mixtures thereof. Examples of natural gums that can be used with the present invention include guar gum, xantham gum, and gum arabic. Preferably, the thickener is used in an amount of about 0.1 to about 2 weight percent based on the total weight of the composition. The thickener can be mixed with water prior to being added. A homogenizer can be used to dissolve xantham gum, guar gum, gum arabic or other natural gums used with the present invention.

Next, in method 400, at least one pH adjusting agent is added to the mixture (step 406). The at least one pH adjusting agent can be selected from the group consisting of sodium hydroxide, potassium hydroxide and mixtures thereof. Preferably, the at least one pH adjusting agent is used in an amount of about 0.01 to about 2 weight percent based on the total weight of the composition.

Next, in method 400, at least one solvent is added to the mixture (step 407). The at least one solvent can exclude water. In preferred embodiments of the invention, the at least one solvent is ethanol. Preferably, the solvent is used in an amount of about 0.2 to about 2 weight percent based on the total weight of the composition. More preferably, the solvent is used in an amount of about 0.5 to about 2 weight percent based on the total weight of the composition.

Next, in method 400, at least one corrosion inhibitor is added to the mixture (step 408). In preferred embodiments of the invention, the at least one corrosion inhibitor is at least one selected from the group consisting of gum arabic, sodium polyaspartate and mixtures thereof. Preferably, the at least one corrosion inhibitor is used in an amount of about 0.1 to about 2.5 weight percent based on the total weight of the composition.

Next, in method 400, at least one preservative is added to the mixture (step 409). Examples of preservatives for use with the present invention include benzoic acid, potassium sorbate, nisin, natamycin, and mixtures thereof. Preferably the preservative is at least one selected from the group consisting of potassium sorbate, nisin, natamycin, and mixtures thereof. Additionally, boric acid, which is suitable for use as a builder in the present invention, can also be used as a preservative in the present invention. The preservative, in addition to boric acid, can be used in an amount of not greater than about 1 weight percent based on the total weight of the composition.

Next, in method 400, at least one essential oil is added to the mixture (step 410).

Figure 5:
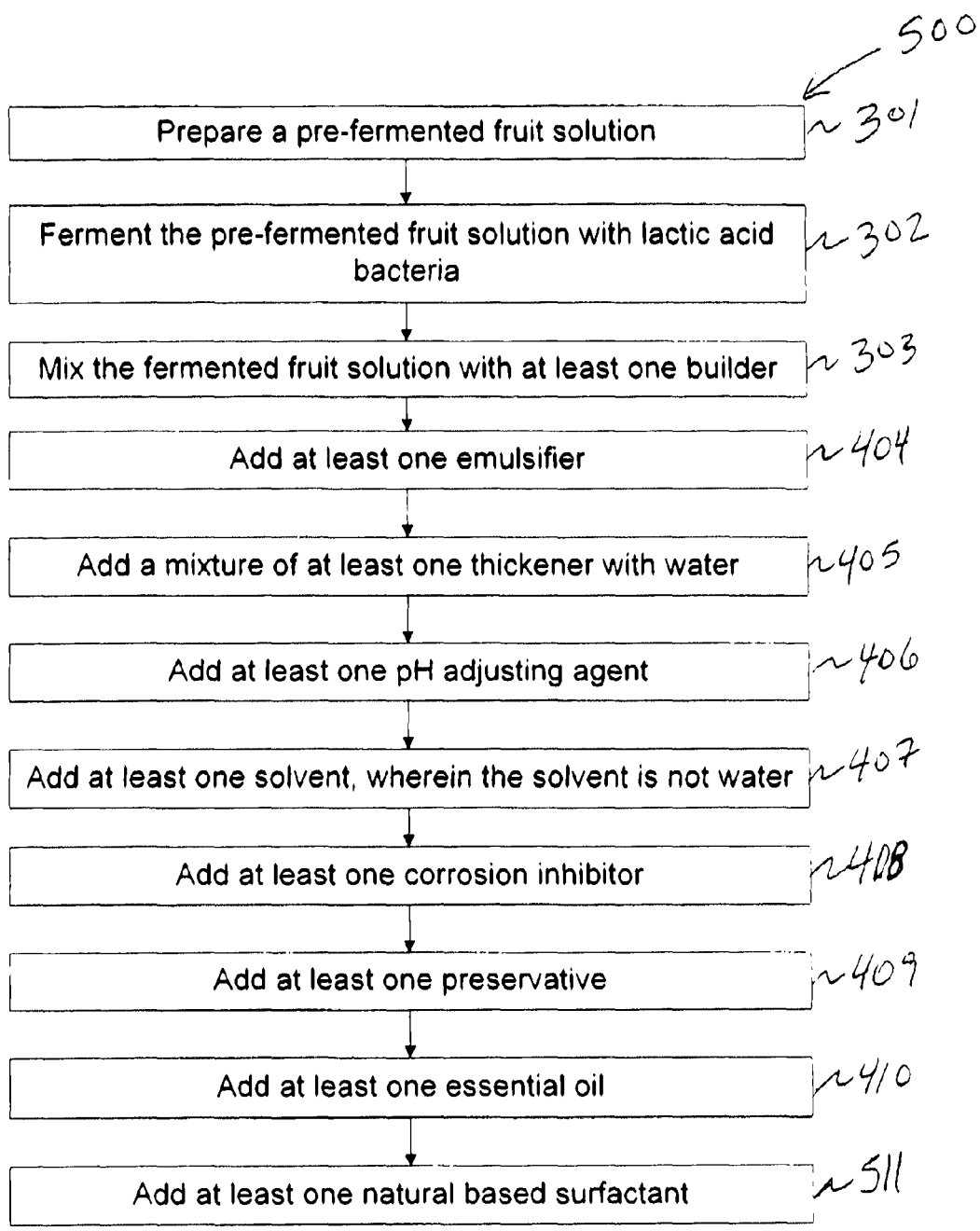
FIG. 5 a flow diagram of a third exemplary method of making cleaning compositions in accordance with exemplary embodiments of the present invention.

Referring now to FIG. 5, a flow diagram illustrating the steps of a method of making cleaning compositions in accordance with exemplary embodiments of the present invention is provided. In an embodiment of the present invention, method 500 includes several of the same steps of method 300, including steps 301, 302, and 303, and method 400, including steps 404, 405, 406, 407, 408, 409 and 410.

Method 500 can further include adding at least one natural based surfactant (step 511). Natural based surfactants include but are not limited to sodium lauryl sulfate, cocamidopropyl betaine, and alkyl polyglycoside. Preferably, the at least one natural based surfactant is selected from the group consisting of sodium lauryl sulfate, cocamidopropyl betaine, alkyl polyglycoside and mixtures thereof. Further, the at least one surfactant can be used in an amount of about 1 to about 23 weight percent based on the total weight of the composition. Preferably, the at least one surfactant can be used in an amount of about 1 to about 15 weight percent based on the total weight of the composition. More preferably, the at least one surfactant can be used in an amount of about 2 to about 15 weight percent based on the total weight of the composition. Even more preferably, the at least one surfactant can be used in an amount of about 5 to about 15 weight percent based on the total weight of the composition.

In certain preferred embodiments of the present invention, the at least one surfactant is sodium lauryl sulfate. In preferred embodiments of the present invention where the surfactant is sodium lauryl sulfate, the sodium lauryl sulfate can be used in an amount of about 1 to about 23 weight percent based on the total weight of the composition. More preferably, in certain preferred embodiments of the present invention where the surfactant is sodium lauryl sulfate, sodium lauryl sulfate can be used in an amount of about 1 to about 15 weight percent based on the total weight of the composition. Even more preferably, in certain preferred embodiments of the present invention where the surfactant is sodium lauryl sulfate, sodium lauryl sulfate can be used in an amount of about 5 to about 15 weight percent based on the total weight of the composition. Most preferably, in certain preferred embodiments of the present invention where the surfactant is sodium lauryl sulfate, sodium lauryl sulfate can be used in an amount of about 8 to about 15 weight percent based on the total weight of the composition.

In other preferred embodiments of the present invention, the at least one natural based surfactant is alkyl polyglycoside. In certain embodiments of the present invention where the surfactant is alkyl polyglycoside, the surfactant can be used in an amount of about 1 to about 23 weight percent based on the total weight of the composition. Preferably, in certain embodiments of the present invention where the surfactant is alkyl polyglycoside, alkyl polyglycoside can be used in an amount of about 1 to about 15 weight percent based on the total weight of the composition. Even more preferably, in certain embodiments of the present invention where the surfactant is alkyl polyglycoside, alkyl polyglycoside can be used in an amount of about 2 to about 8 weight percent based on the total weight of the composition. Most preferably, in certain embodiments of the present invention where the surfactant is alkyl polyglycoside, alkyl polyglycoside can be used in an amount of about 5 to about 6.5 weight percent based on the total weight of the composition.

Embodiments of the present invention also include methods of cleaning an article with a cleaning composition comprising a fermented fruit solution and a builder. Following preparation of the cleaning compositions described above, the cleaning compositions can be used to clean an article. Additionally, the cleaning compositions can be used to launder an article or to clean stains from an article. Even more, the cleaning compositions can be used as a surface cleaner. For example, the cleaning compositions of the present invention can be used to clean floors, countertops or other types of surfaces and the like.

The following examples illustrate certain embodiments of the invention without limitation.

EXAMPLES

Fermented fruit solutions were prepared in accordance with the methods described in detail above. The fermented fruit solutions were prepared similarly except for the composition of the pre-fermented fruit solution. Table 1 provides the components of Examples 1-3:

TABLE 1

|  | Example 1 | Example 2 | Example 3 |
| --- | --- | --- | --- |
| Sucrose | 12.5% | 11.1% | 10% |
| Pineapple Puree | 37.5% | 33.3% | 30% |
| Water | 50.0% | 55.6% | 60% |

All concentrations are weight percent, based on the total weight of the pre-fermented fruit composition.

After preparation of the fermented fruit solutions, the pH, total sugar content and total acid content was measured after 2.5 months. Three different samples of each example were measured. The results of these measurements are provided in Table 2.

TABLE 2

|  | pH | Total Sugar Content (%) | Total Acid Content (%) |
| --- | --- | --- | --- |
| Example 1A | 3.09 | 0.04 | 3.19 |
| Example 1B | 3.19 | 0.03 | 3.07 |
| Example 1C | 3.17 | 1.62 | 3.10 |
| Example 2A | 3.11 | 1.40 | 3.06 |
| Example 2B | 3.08 | 0.10 | 2.28 |
| Example 2C | 3.15 | 0.11 | 2.28 |
| Example 3A | 3.11 | 0.13 | 2.27 |
| Example 3B | 3.16 | 0.15 | 2.25 |
| Example 3C | 3.13 | 0.14 | 2.26 |

As is illustrated in Table 2, the total acid content of Example 1 was surprisingly higher than the total acid content of the other examples. Thus, it appears that the weight percents of sucrose, pineapple and water, as used in Example 1 of the present invention result in superior cleaning compositions. Specifically, a ratio of sugar:fruit:water of 1:3:4 appears to produce superior cleaning compositions.

Additional fermented fruit solutions were prepared in accordance with the methods described in detail above. In Examples 4-33, the pre-fermented fruit solutions were all prepared using a sugar:fruit:water ratio of 1:3:4. In Examples 4-18, the initial brix level of the pineapple used to prepare the pineapple puree was not measured. Rather, all pineapples, regardless of brix level were used for Examples 4-18. In Examples 19-33, the selected pineapples included a brix level of greater than or equal to 12%.

The initial brix level of the pre-fermented fruit solution was measured at day 0. After preparation of the fermented fruit solutions, the pH, total sugar content ("TS") and total acid content ("TA") of the fermented fruit solutions were measured after 1.5 months. Additionally, the pH and total acid content ("TA") of the fermented fruit solutions were measured after 2 months. Finally, the pH, total acid content ("TA"), electric conductivity ("EC") and temperature of the fermented fruit solutions were measured after 3 months. The results of these measurements are provided in Table 3.

TABLE 3

| Example No. | Day 0 Brix Level (%) | pH | 1.5 Months TS (%) | TA (%) | 2 Months pH | TA (%) | 3 Months pH | TA (%) | EC (μS) | Temp (° C.) |
|---|---|---|---|---|---|---|---|---|---|---|
| 4 | 16.0 | 2.90 | 0.02 | 3.51 | 3.10 | 3.47 | 3.00 | 3.38 | 2570 | 33.0 |
| 5 | 16.7 | 3.00 | 0.05 | 2.84 | 3.00 | 3.47 | 3.00 | 3.15 | 2540 | 33.0 |
| 6 | 13.0 | 3.00 | 0.04 | 3.15 | 3.10 | 3.11 | 3.00 | 3.38 | 2700 | 32.5 |
| 7 | 12.9 | 2.90 | 0.02 | 3.78 | 3.10 | 3.96 | 3.00 | 3.60 | 2550 | 33.0 |
| 8 | 13.0 | 3.00 | 0.03 | 3.06 | 3.20 | 3.51 | 3.00 | 3.06 | 2400 | 33.0 |
| 9 | 14.9 | 3.00 | 0.07 | 3.24 | 3.00 | 3.69 | 3.00 | 3.74 | 2680 | 33.0 |
| 10 | 15.0 | 3.00 | 0.00 | 3.42 | 3.20 | 3.33 | 3.00 | 3.65 | 2630 | 33.0 |
| 11 | 14.2 | 3.00 | 0.00 | 3.15 | 3.10 | 3.87 | 3.00 | 3.38 | 2620 | 33.0 |
| 12 | 14.6 | 3.00 | 0.06 | 3.11 | 3.00 | 3.78 | 3.00 | 3.69 | 2660 | 32.5 |
| 13 | 14.8 | 3.00 | 0.03 | 3.38 | 3.00 | 3.33 | 3.00 | 3.42 | 2730 | 32.5 |
| 14 | 15.8 | 3.00 | 0.03 | 3.42 | 3.10 | 3.87 | 3.00 | 3.60 | 2560 | 33.0 |
| 15 | 18.0 | 3.00 | 0.04 | 3.42 | 3.00 | 3.74 | 3.00 | 3.56 | 2250 | 32.5 |
| 16 | 14.0 | 3.00 | 0.04 | 3.47 | 3.10 | 3.33 | 3.00 | 3.47 | 2730 | 32.5 |
| 17 | 13.7 | 2.90 | 0.02 | 3.51 | 3.00 | 3.29 | 3.00 | 4.23 | 2640 | 32.5 |
| 18 | 13.4 | 3.00 | 0.03 | 3.42 | 3.10 | 4.01 | 3.00 | 3.29 | 2660 | 32.5 |
| 19 | 16.0 | 3.09 | 0.04 | 2.97 | 3.00 | 3.96 | 3.10 | 3.69 | 2910 | 30.0 |
| 20 | 16.8 | 3.08 | 0.04 | 3.38 | 3.00 | 4.05 | 3.10 | 4.23 | 3210 | 30.0 |
| 21 | 16.7 | 3.04 | 0.04 | 3.78 | 3.00 | 4.23 | 3.00 | 4.82 | 2880 | 30.0 |
| 22 | 15.8 | 3.03 | 0.04 | 3.24 | 3.00 | 4.32 | 3.10 | 5.54 | 3270 | 30.0 |
| 23 | 14.6 | 2.95 | 0.04 | 3.65 | 3.00 | 4.19 | 3.10 | 5.27 | 2990 | 30.0 |
| 24 | 16.7 | 2.96 | 0.04 | 4.41 | 3.00 | 4.05 | 3.10 | 5.27 | 3110 | 30.0 |
| 25 | 17.8 | 2.92 | 0.03 | 4.59 | 2.70 | 4.50 | 3.00 | 4.59 | 2980 | 30.0 |
| 26 | 16.3 | 2.98 | 0.05 | 3.60 | 2.90 | 4.14 | 3.00 | 4.73 | 2790 | 30.0 |
| 27 | 17.5 | 2.92 | 0.03 | 3.60 | 2.90 | 3.78 | 3.10 | 4.19 | 2900 | 30.0 |
| 28 | 18.3 | 2.93 | 0.03 | 4.01 | 2.90 | 3.56 | 3.00 | 5.63 | 2940 | 30.0 |
| 29 | 18.6 | 2.92 | 0.05 | 4.37 | 3.00 | 4.10 | 3.10 | 4.86 | 2910 | 30.0 |
| 30 | 17.5 | 2.93 | 0.04 | 4.23 | 3.00 | 3.78 | 3.10 | 4.77 | 3040 | 30.0 |
| 31 | 16.3 | 2.94 | 0.04 | 4.41 | 3.00 | 3.69 | 3.00 | 4.10 | 3090 | 30.0 |
| 32 | 17.6 | 2.90 | 0.05 | 4.41 | 2.90 | 4.19 | 3.00 | 5.67 | 2970 | 30.0 |
| 33 | 16.6 | 2.97 | 0.02 | 3.96 | 3.00 | 3.96 | 3.00 | 4.32 | 3050 | 30.0 |

As is illustrated in Table 3, the total acid content of Examples 19-33 was surprisingly higher than the total acid content of the other examples. In Examples 4-18, the total acid content after 3 months ranged from 3.06% to 4.23% with a mean value of 3.50%. In Examples 19-33, the total acid content after 3 months ranged from 3.69% to 5.67% with a mean value of 4.77%. Thus, the selection of pineapples for the fruit puree with a brix level greater than or equal to 12% results in superior cleaning compositions.

Additional fermented fruit solutions were prepared in accordance with the methods described in detail above. In Examples 34-48, the selected pineapples were washed only with tap water. In Examples 49-63, the selected pineapples were all washed with previously created fermented fruit solutions.

After preparation of the fermented fruit solutions, the pH and brix level were measured at day 0. Additionally, the pH and total acid content ("TA") were measured after 2 days. The pH, total sugar content ("TS"), total acid content ("TA"), and electrical conductivity ("EC") were measured after 1 month. The results of these measurements are provided in Table 4.

TABLE 4

| Example No. | Day 0 pH | Brix Level (%) | Day 2 pH | TA (%) | 1 Month pH | TS (%) | TA (%) | EC (μS) |
|---|---|---|---|---|---|---|---|---|
| 34 | 8.10 | 17.9 | 4.00 | 0.77 | 3.00 | 0.0000 | 2.97 | 3670 |
| 35 | 8.10 | 18.2 | 4.00 | 0.85 | 3.00 | 0.0042 | 3.60 | 3190 |
| 36 | 8.00 | 17.6 | 4.00 | 0.85 | 2.93 | 0.0032 | 3.42 | 3040 |
| 37 | 8.40 | 17.6 | 4.00 | 0.77 | 3.00 | 0.0039 | 2.97 | 3160 |
| 38 | 8.30 | 17.6 | 4.00 | 0.85 | 3.00 | 0.0000 | 2.70 | 3700 |
| 39 | 8.20 | 17.9 | 4.00 | 1.08 | 3.00 | 0.0032 | 4.50 | 3010 |
| 40 | 8.20 | 17.9 | 4.00 | 0.90 | 3.00 | 0.0042 | 3.60 | 3160 |
| 41 | 8.50 | 17.6 | 4.00 | 1.13 | 2.90 | 0.0004 | 3.15 | 3030 |
| 42 | 7.10 | 17.2 | 4.00 | 1.04 | 3.00 | 0.0056 | 3.29 | 3490 |
| 43 | 7.40 | 17.9 | 4.00 | 1.04 | 3.00 | 0.0046 | 3.11 | 2950 |
| 44 | 6.40 | 17.2 | 4.00 | 1.04 | 3.00 | 0.0011 | 3.78 | 3820 |
| 45 | 7.10 | 17.8 | 4.00 | 0.68 | 3.00 | 0.0042 | 3.15 | 3640 |
| 46 | 6.70 | 17.2 | 4.00 | 0.63 | 3.00 | 0.0001 | 3.51 | 3610 |
| 47 | 6.70 | 17.6 | 4.00 | 1.26 | 3.00 | 0.0022 | 3.15 | 3420 |
| 48 | 7.40 | 17.7 | 4.00 | 1.22 | 3.00 | 0.0000 | 3.51 | 3540 |
| 49 | 6.70 | 18.6 | — | — | 3.10 | 0.0404 | 5.22 | 3910 |
| 50 | 7.00 | 18.2 | 3.40 | 3.33 | 3.10 | 0.0369 | 4.14 | 3830 |
| 51 | 6.40 | 18.0 | — | — | 3.00 | 0.0321 | 5.04 | 3550 |
| 52 | 6.20 | 17.7 | 3.48 | 3.87 | 3.00 | 0.0547 | 4.32 | 3050 |
| 53 | 6.40 | 17.7 | — | — | 3.10 | 0.0415 | 4.86 | 3600 |
| 54 | 6.10 | 17.5 | 3.50 | 2.07 | 3.00 | 0.0373 | 5.22 | 3560 |
| 55 | 6.10 | 17.5 | 3.40 | 3.24 | 3.00 | 0.0356 | 4.95 | 3440 |
| 56 | 6.20 | 17.8 | — | — | 3.10 | 0.0392 | 5.40 | 3600 |
| 57 | 6.40 | 18.3 | — | — | 3.10 | 0.0356 | 4.68 | 3970 |
| 58 | 6.30 | 17.3 | 3.50 | 1.71 | 3.10 | 0.0317 | 5.04 | 3890 |
| 59 | 6.40 | 17.7 | — | — | 3.10 | 0.0331 | 4.14 | 3950 |
| 60 | 6.20 | 17.7 | — | — | 3.00 | 0.0411 | 5.04 | 3490 |
| 61 | 6.30 | 17.5 | 3.43 | 2.79 | 3.00 | 0.0380 | 5.04 | 3790 |
| 62 | 6.10 | 17.5 | 3.46 | 2.16 | 3.00 | 0.0432 | 5.22 | 3540 |
| 63 | 6.10 | 17.6 | 3.50 | 2.70 | 3.00 | 0.0394 | 4.86 | 3900 |

As is illustrated in Table 4, the total acid content of Examples 49-63 was surprisingly higher than the total acid content of the other examples. In Examples 34-48, the total acid content after 1 month ranged from 2.70% to 4.50% with a mean value of 3.36%. In Examples 49-63, the total acid content after 1 month ranged from 4.14% to 5.40% with a mean value of 4.88%. Thus, cleaning the selected pineapples with a previously created fermented fruit solution rather than cleaning the selected pineapples with water results in superior cleaning compositions.

The present invention also provides for cleaning compositions comprising fermented fruit solutions and builders. The cleaning compositions of the present invention have cleaning capabilities that are similar to or better than petroleum based products. A significant number of tests were conducted to determine the capabilities of the present invention to launder an article and to clean a stain from an article. The compositions of the present invention clean on par with or better than leading petroleum linked mass market products.

In certain tests, cleaning compositions of the present invention were compared against leading brand name laundry detergent products. Additionally, cleaning compositions of the present invention were compared against leading stain remover products.

In the below described tests (represented in Tables 5-18), the following study methodology was used. In all experiments, stains were created on white cotton pieces (each 10×10 cm), which were attached to a white cotton towel. The stains were all created at the same time in an effort to create consistent stains for each test product. In the experiment with results depicted in Table 5 below, four stains were examined. The four stains examined were: (1) blood; (2) ground soil; (3) carbon with palm oil; and (4) clay with pig fat (this stain was used to approximate sweat with mixed dust/pollution in the air). In the experiments with results depicted in Tables 6-16, ten stains were examined. The ten stains examined were: (1) blood; (2) grass; (3) dark ground soil; (4) coffee; (5) soy sauce; (6) carbon with palm oil (this stain was used to approximate cooking oil stains); (7) clay with pig fat (this stain was used to approximate sweat with mixed dust/pollution in the air); (8) clay with water (this stain was used to approximate dust/pollution in the air); (9) make-up (this stain was used to approximate a typical stain created by a person wearing make-up); and (10) red wine. In the experiment with results depicted in Table 17, nine stains were examined. The nine stains examined were the same as the previously described ten stains with two exceptions. First, the clay with water stain (i.e., stain (8)) was not used. Second, the clay with pig fat stain (i.e., stain (7)) was replaced with a different stain used to approximate sweat. The new stain was prepared using the following ingredients:

| Stain 7 | |
|---|---|
| Palmetic acid | 10.0% |
| Stearic acid (powder) | 5.0% |
| Soybean oil | 19.8% |
| Carnauba wax | 15.0% |
| Paraffin oil | 10.0% |
| Olive oil | 25.0% |
| Oleic acid | 15.0% |
| Carbon | 0.2% |
| Total | 100.0% |

In the experiment with results depicted in Table 18, seven stains were examined. The seven stains examined were the same as the previously described nine stains (including the new stain 7), with two exceptions. The two stains: (i) carbon with palm oil (i.e., stain (6) noted above) and (ii) make-up (i.e., stain (9) noted above) were not used.

After creating the stains, the stained towel was washed with two other white cotton towels using an amount of 35 mL of each test detergent product. Standard washing machines (Brand: Electrolux; model: Time Manager) were used on cotton setting at a spin cycle of 500. A color analyzer (model no. RGB-1002) was used to determine a numerical value representative of each of red, green, and blue color (on the device, red values range from 0 to 1023 ("R"); green values range from 0 to 1023 ("G"); blue values range from 0 to 1023 ("B")), for each type of stain. The higher the number, the whiter the object is—pure white cloth would have an approximate numerical value of R=1023, G=1023, B=1023. Stains were measured with the color analyzer both before the wash and after the wash; there are three numerical values for each stain (R, G, B). For example, for 10 stains, there are 30 total measurements of the stain before the wash, and 30 total measurements of the stain after the wash. The 30 total measurements of the stain before the wash were added together, and the 30 total measurements of the stain after the wash were added together. The difference between the sum of the measurements after the wash and the sum of the measurements before the wash was calculated and represents the "cleaning value" of the cleaning composition. The larger the difference in numerical values (i.e., the larger the cleaning value), the more the stain had been removed, and the cleaner the cloth. As indicated in the description of each experiment, certain washing experiments were conducted in ambient water temperature (25° C. to 35° C. in Thailand) (setting used on washing machines was the cold cotton setting). Other washing experiments, as indicated, were conducted at warm water temperature settings of 60° C. (setting used on washing machines was the 60° C. cotton setting).

While the absolute numerical values are not necessarily comparable, differences in cleaning values are comparable (note that for each experiment, stains were made at the same time). Thus, cleaning values were the reported results for each study. In addition to determining cleaning values, the results were examined visually. The cleaning values, however, were determined to be more reliable than the visual results.

In one experiment, different compositions containing different surfactants were compared. Six different compositions were examined comprising either 90% of fermented fruit solution or water and 10% of one of three surfactants. In this study, ambient water temperature conditions were used. Additionally, only four stains were examined: (1) blood; (2) ground soil; (3) carbon with palm oil; and (4) clay with pig fat. The results of the study are provided in Table 5.

TABLE 5

| Laundry Detergent Composition | Cleaning Value |
|---|---|
| 90% Fermented Fruit Solution 10% Cocamidopropyl Betaine | 2076 |
| 90% Water 10% Cocamidopropyl Betaine | 1065 |
| 90% Fermented Fruit Solution 10% Alkyl Polyglycoside | 1556 |
| 90% Water 10% Alkyl Polyglycoside | 1172 |
| 90% Fermented Fruit Solution 10% Sodium Lauryl Sulfate | 1866 |
| 90% Water 10% Sodium Lauryl Sulfate | 1793 |

As indicated by the above table, all three surfactants examined—cocamidopropyl betaine, alkyl polyglycoside, and sodium lauryl sulfate—worked synergistically with fermented fruit solution. In all three instances, the fermented fruit solution in combination with the surfactant produced superior results to water in combination with the surfactant. That is fermented fruit solution in combination with a natural based surfactant produced superior cleaning abilities to water with a natural based surfactant.

Additional embodiments of the present invention were prepared using further additives. In addition to surfactants, additives such as boric acid, sodium citrate, thickeners, sodium polyaspartate, oleic acid, lactic acid, sodium bicarbonate, ethanol, glycerol, citric acid, hydrogen peroxide, essential oil, preservatives, pH adjusting agents, etc. were used. Exemplary embodiments created for testing include Example 64, Example 65, Example 66, Example 67, Example 68, Example 69, Example 70, Example 71, Example 72, Example 73, Example 74, Example 75, Example 76, Example 77, Example 78, Example 79, Example 80, Example 81, Example 82, Example 83, Example 84, Example 85 and Example 86. These exemplary embodiments are set forth below

Example 64

| Ingredient | % in solution |
| --- | --- |
| Water | 32.1% |
| Sodium bicarbonate | 1.6% |
| Sodium citrate | 0.8% |
| Citric acid | 0.4% |
| Boric acid | 0.8% |
| Alkyl polyglycoside | 6.4% |
| Cocamidopropyl betaine | 16.1% |
| Sodium chloride | 1.6% |
| Fermented fruit | 36.1% |
| Ethanol | 4.0% |
| Total | 100.0% |

Example 65

| Ingredient | % in solution |
| --- | --- |
| Fermented fruit | 42.2% |
| Sodium citrate | 2.1% |
| Boric acid | 2.1% |
| Oleic acid | 1.1% |
| Glycerol | 1.4% |
| Sodium lauryl sulfate | 21.1% |
| Ethanol | 1.4% |
| Water | 28.1% |
| Sodium Chloride | 0.4% |
| Total | 100.0% |

Example 66

| Ingredient | % in solution |
| --- | --- |
| Fermented fruit | 41.8% |
| Sodium citrate | 2.1% |
| Boric acid | 2.1% |
| Oleic acid | 1.1% |
| Glycerol | 1.4% |
| Sodium lauryl sulfate | 20.9% |
| Alkyl polyglycoside | 1.4% |
| Ethanol | 1.4% |
| Water | 27.9% |
| Total | 100.0% |

Example 67

| Ingredient | % in solution |
| --- | --- |
| Fermented fruit | 47.4% |
| Xanthan Gum | 0.5% |
| Sodium citrate | 4.7% |
| Boric acid | 2.7% |
| Oleic acid | 1.1% |
| Glycerol | 1.4% |
| Sodium lauryl sulfate | 10.1% |
| Ethanol | 1.4% |
| Water | 30.4% |
| Sodium Chloride | 0.3% |
| Total | 100.0% |

Example 68

| Ingredient | % solution |
| --- | --- |
| Fermented fruit | 64.4% |
| Xanthan Gum | 0.6% |
| Sodium citrate | 17.2% |
| Boric acid | 4.3% |
| Alkyl polyglycoside | 8.6% |
| Sodium chloride | 1.3% |
| Polyaspartate | 0.9% |
| Ethanol | 0.9% |
| Glycerol | 1.8% |
| Total | 100.0% |

Example 69

| Ingredient | % in solution |
| --- | --- |
| Fermented fruit | 67.5% |
| 50% KOH | 2.0% |
| Xanthan Gum | 0.7% |
| Sodium citrate | 18.0% |
| Boric acid | 4.5% |
| Alkyl polyglycoside | 2.2% |
| Sodium chloride | 1.3% |
| Polyaspartate | 0.9% |
| Ethanol | 0.9% |
| Glycerol | 1.9% |
| Total | 100.0% |

Example 70

| Ingredient | % in solution |
|---|---|
| Fermented fruit | 72.2% |
| Xanthan Gum | 0.7% |
| Sodium citrate | 14.4% |
| Boric acid | 4.8% |
| alkyl polyglycoside | 2.4% |
| Sodium chloride | 1.4% |
| Polyaspartate | 1.0% |
| Ethanol | 1.0% |
| Glycerol | 2.0% |
| Total | 100.0% |

Example 71

| Ingredient | % in solution |
|---|---|
| Fermented fruit | 37.6% |
| Xanthan Gum | 1.0% |
| Sodium citrate | 1.9% |
| Boric acid | 1.9% |
| Oleic acid | 1.0% |
| Glycerol | 1.3% |
| Sodium lauryl sulfate | 18.8% |
| Ethanol | 1.3% |
| Water | 25.1% |
| Sodium Chloride | 0.3% |
| Hydrogen peroxide | 9.9% |
| Total | 100.0% |

Example 72

| Ingredient | % in solution |
|---|---|
| Fermented fruit | 24.6% |
| Lactic acid | 0.6% |
| Sodium polyaspartate | 0.4% |
| Guar Gum | 0.5% |
| Sodium citrate | 1.2% |
| Boric acid | 6.2% |
| Glycerol | 1.2% |
| Sodium lauryl sulfate | 15.4% |
| Ethanol | 0.6% |
| Water | 49.3% |
| Total | 100.0% |

Example 73

| Ingredient | % in solution |
|---|---|
| Fermented fruit | 25.9% |
| Lactic acid | 1.9% |
| Sodium polyaspartate | 0.4% |
| Xanthan Gum | 0.5% |
| Sodium citrate | 1.3% |
| Boric acid | 6.5% |
| Glycerol | 1.3% |
| Sodium lauryl sulfate | 9.7% |
| Ethanol | 0.6% |
| Water | 51.8% |
| Total | 100.0% |

Example 74

| Ingredient | % in solution |
|---|---|
| Fermented fruit | 22.0% |
| KOH | 0.9% |
| Lactic acid | 0.5% |
| Sodium polyaspartate | 0.3% |
| Guar Gum | 0.4% |
| Sodium citrate | 1.1% |
| Boric acid | 4.4% |
| Glycerol | 1.1% |
| Sodium lauryl sulfate | 13.7% |
| Ethanol | 0.5% |
| Water | 54.9% |
| Potassium sorbate | 0.1% |
| Total | 100.0% |

Example 75

| Ingredient | % in solution |
|---|---|
| Fermented fruit | 25.1% |
| KOH | 0.7% |
| Xantham Gum | 0.1% |
| Sodium citrate | 20.9% |
| Boric acid | 2.1% |
| Water | 41.8% |
| Alkyl polyglucoside | 6.3% |
| Sodium polyaspartate | 1.7% |
| Ethanol | 0.6% |
| Glycerol | 0.8% |
| Total | 100.0% |

Example 76

| Ingredient | % in solution |
|---|---|
| Fermented fruit | 25.4% |
| Sodium polyaspartate | 2.5% |
| KOH | 0.6% |
| Guar Gum | 0.3% |
| Sodium citrate | 16.9% |
| Boric acid | 3.4% |
| Water | 42.3% |
| Alkyl polyglucoside | 6.3% |
| Ethanol | 0.8% |
| Glycerol | 1.3% |
| Total | 100.0% |

Example 77

| Ingredient | % in solution |
|---|---|
| Fermented fruit | 27.1% |
| Sodium polyaspartate | 2.3% |
| KOH | 0.7% |
| Guar Gum | 0.4% |
| Sodium citrate | 18.0% |
| Boric acid | 2.0% |
| Water | 40.6% |
| Alkyl polyglucoside | 6.8% |

-continued

| Ingredient | % in solution |
|---|---|
| Ethanol | 0.9% |
| Glycerol | 1.4% |
| Total | 100.0% |

Example 78

| Ingredient | % in solution |
|---|---|
| Fermented fruit | 30.4% |
| Sodium polyaspartate | 2.3% |
| KOH | 0.7% |
| Guar Gum | 0.3% |
| Sodium citrate | 17.4% |
| Boric acid | 1.0% |
| Water | 39.1% |
| Alkyl polyglucoside | 6.5% |
| Ethanol | 0.9% |
| Glycerol | 1.3% |
| Total | 100.0% |

Example 79

| Ingredient | % in solution |
|---|---|
| Fermented fruit | 40.0% |
| Sodium citrate | 25.0% |
| Boric acid | 2.1% |
| Alkyl polyglucoside | 6.3% |
| KOH | 0.3% |
| Xantham Gum | 0.1% |
| Sodium polyaspartate | 1.7% |
| Ethanol | 0.6% |
| Glycerol | 0.8% |
| Water | 23.1% |
| Total | 100.0% |

Example 80

| Ingredient | % in solution |
|---|---|
| Fermented fruit | 25.0% |
| Sodium citrate | 20.8% |
| Alkyl polyglucoside | 6.3% |
| Xantham Gum | 0.1% |
| Sodium polyaspartate | 1.7% |
| Ethanol | 0.6% |
| Glycerol | 0.8% |
| Water | 44.7% |
| Total | 100.0% |

Example 81

| Ingredient | % in solution |
|---|---|
| Fermented fruit | 40.1% |
| KOH | 1.5% |
| Guar Gum | 0.4% |

-continued

| Ingredient | % in solution |
|---|---|
| Sodium citrate | 20.9% |
| Boric acid | 2.1% |
| Water | 32.5% |
| Sodium polyaspartate | 1.7% |
| Ethanol | 0.6% |
| Glycerol | 0.2% |
| Total | 100.0% |

Example 82

| Ingredient | % in solution |
|---|---|
| Fermented fruit | 40.0% |
| Sodium citrate | 20.8% |
| Boric acid | 2.1% |
| Alkyl polyglucoside | 6.3% |
| KOH | 0.7% |
| Xantham Gum | 0.1% |
| Sodium polyaspartate | 1.7% |
| Ethanol | 0.6% |
| Glycerol | 0.8% |
| Water | 26.9% |
| Total | 100.0% |

Example 83

| Ingredient | % in solution |
|---|---|
| Fermented fruit | 75.1% |
| Xantham Gum | 0.8% |
| KOH | 1.0% |
| Sodium bicarbonate | 10.0% |
| Sodium citrate | 5.0% |
| Alkyl polyglycoside | 2.5% |
| Sodium chloride | 1.5% |
| Sodium polyaspartate | 1.1% |
| Ethanol | 1.0% |
| Glycerol | 2.1% |
| Total | 100.0% |

Example 84

| Ingredient | % in solution |
|---|---|
| Fermented fruit | 40.0% |
| Sodium citrate | 16.0% |
| Alkyl polyglycoside | 5.0% |
| KOH | 0.9% |
| Xantham Gum | 0.1% |
| Polyaspartate | 1.7% |
| Ethanol | 0.6% |
| Glycerol | 0.8% |
| Water | 34.9% |
| Total | 100.0% |

Example 85

| Ingredient | % in solution |
|---|---|
| Fermented fruit | 32.5% |
| Sodium citrate | 18.0% |
| KOH | 0.8% |
| Xantham Gum | 0.1% |
| Polyaspartate | 1.7% |
| Ethanol | 0.6% |
| Glycerol | 0.8% |
| Water | 45.5% |
| Total | 100.0% |

Example 86

| Ingredient | % in solution |
|---|---|
| Fermented fruit | 32.5% |
| Sodium citrate | 16.0% |
| Alkyl polyglycoside | 5.0% |
| Xantham Gum | 0.1% |
| Polyaspartate | 1.7% |
| Ethanol | 0.6% |
| Glycerol | 0.8% |
| Water | 43.3% |
| Total | 100.0% |

Throughout this application, the names: (1) LD Brand 1; (2) LD Brand 2; (3) LD Brand 3; (4) LD Brand 4; (5) LD Brand 5 and (6) LD Brand 6 refer to brand name laundry detergents. LD Brand 1 is a leading brand in Asia and contains linear alkylbenzene sulfonates ("LAS") as a surfactant. Although LAS do not biodegrade anaerobically and can be toxic to marine life, LAS is considered to be a strong and effective surfactant and laundry care products made with LAS can be very effective in their cleaning ability. Therefore, primary comparisons were made to LD Brand 1 in terms of cleaning ability of the invention. LD Brand 3, LD Brand 4 and LD Brand 5 are leading brands in the United States and elsewhere. LD Brand 2 and LD Brand 6 are small brands local to Asia. Also throughout this application, the names: (1) SR Brand 1; (2) SR Brand 2; (3) SR Brand 3; and (4) SR Brand 4 refer to leading brand name laundry stain remover products.

In Table 6, the cleaning ability of an exemplary embodiment, Example 64, was compared to five brand name laundry detergents: (1) LD Brand 1; (2) LD Brand 2; (3) LD Brand 3; (4) LD Brand 4; and (5) LD Brand 5. In this study, ambient water temperature conditions were used. Additionally, all ten stains were examined. The results of the study are provided in Table 6.

TABLE 6

| Laundry Detergent Composition | Cleaning Value |
|---|---|
| Example 64 | 5606 |
| LD Brand 1 | 5802 |
| LD Brand 2 | 3388 |
| LD Brand 3 | 5166 |
| LD Brand 4 | 5447 |
| LD Brand 5 | 5394 |

As is illustrated by the above table, laundry detergents of the present invention produced cleaning results that are comparable to and better than brand name laundry detergents.

In Table 7, the cleaning ability of an exemplary embodiment, Example 65, was compared to four brand name laundry detergents: (1) LD Brand 1; (2) LD Brand 2; (3) LD Brand 3; and (4) LD Brand 4. In this study, ambient water temperature conditions were used. Additionally, all ten stains were examined.

TABLE 7

| Laundry Detergent Composition | Cleaning Value |
|---|---|
| Example 65 | 6261 |
| LD Brand 1 | 6492 |
| LD Brand 2 | 5274 |
| LD Brand 3 | 5449 |
| LD Brand 4 | 6329 |

As is illustrated by the above table, laundry detergents of the present invention produced cleaning results that are comparable to and better than brand name laundry detergents.

In Table 8, the cleaning ability of two exemplary embodiments, Example 65 and Example 66, were compared to five brand name laundry detergents: (1) LD Brand 1; (2) LD Brand 2; (3) LD Brand 3; (4) LD Brand 4; and (5) LD Brand 6. In this study, warm temperature conditions were used. Additionally, all ten stains were examined.

TABLE 8

| Laundry Detergent Composition | Cleaning Value |
|---|---|
| Example 65 | 7328 |
| Example 66 | 7338 |
| LD Brand 1 | 6496 |
| LD Brand 2 | 5467 |
| LD Brand 3 | 5865 |
| LD Brand 4 | 6027 |
| LD Brand 6 | 5001 |

As is illustrated by the above table, laundry detergents of the present invention produced superior cleaning results than each of the brand name laundry detergents examined.

In Table 9, the cleaning ability of an exemplary embodiment, Example 67, Example 68 and Example 69 and Example 70 were compared to two brand name laundry detergents: (1) LD Brand 1; and (2) LD Brand 3. In this study, both ambient and warm water temperature conditions were used. Additionally, all ten stains were examined.

TABLE 9

| Laundry Detergent Composition | Cleaning Value |
|---|---|
| Example 67 - ambient temperature conditions | 6887 |
| Example 67 - warm temperature conditions | 6699 |
| Example 68 - ambient temperature conditions | 6543 |
| Example 68 - warm temperature conditions | 6485 |
| Example 69 - ambient temperature conditions | 6161 |
| Example 70 - ambient temperature conditions | 6095 |
| LD Brand 1 - ambient temperature conditions | 6453 |
| LD Brand 1 - warm temperature conditions | 6843 |
| LD Brand 3 - ambient temperature conditions | 5543 |
| LD Brand 3 - warm temperature conditions | 5715 |

As is illustrated by the above table, laundry detergents of the present invention produced cleaning results that were comparable to or better than the cleaning results of the brand name laundry detergents examined at both ambient water temperature conditions and warm water temperature conditions.

In Table 10, the cleaning ability of an exemplary embodiment, Example 67, was compared to four brand name laundry detergents: (1) LD Brand 1; (2) LD Brand 2; (3) LD Brand 3; and (4) LD Brand 4. In this study, both ambient and warm water temperature conditions were used. Additionally, all ten stains were examined.

TABLE 10

| Laundry Detergent Composition | Cleaning Value |
| --- | --- |
| Example 67 - ambient temperature conditions | 5955 |
| Example 67 - warm temperature conditions | 6386 |
| LD Brand 1 - ambient temperature conditions | 5931 |
| LD Brand 1 - warm temperature conditions | 6075 |
| LD Brand 2 - ambient temperature conditions | 5491 |
| LD Brand 2 - warm temperature conditions | 5105 |
| LD Brand 3 - ambient temperature conditions | 5903 |
| LD Brand 3 - warm temperature conditions | 6124 |
| LD Brand 4 - ambient temperature conditions | 5821 |
| LD Brand 4 - warm temperature conditions | 5780 |

As is illustrated by the above table, laundry detergents of the present invention produced cleaning results that were comparable to or better than the cleaning results of the brand name laundry detergents examined at ambient water temperature conditions and warm water temperature conditions.

Experiments were also conducted to evaluate laundry detergents of the present invention in comparison to brand name stain remover products. In Table 11, the cleaning ability of an exemplary embodiment, Example 71, was compared to four brand name stain removers: (1) SR Brand 1; (2) SR Brand 2; (3) SR Brand 3; and (4) SR Brand 4. In this study, ambient water temperature conditions were used. Additionally, all ten stains were examined.

TABLE 11

| Laundry Detergent Composition | Cleaning Value |
| --- | --- |
| Example 71 | 6166 |
| SR Brand 1 | 6293 |
| SR Brand 2 | 5795 |
| SR Brand 3 | 6277 |
| SR Brand 4 | 6152 |

As is illustrated by the above table, laundry detergents of the present invention produced cleaning results that were comparable to or better than the cleaning results of the brand name stain removers examined at ambient water temperature conditions.

In Table 12, the cleaning ability of two exemplary embodiments, Example 72 and Example 73, were compared to four brand name stain removers: (1) SR Brand 1; (2) SR Brand 2; (3) SR Brand 3; and (4) SR Brand 4. In this study, both ambient and warm water temperature conditions were used. Additionally, all ten stains were examined.

TABLE 12

| Laundry Detergent Composition | Cleaning Value |
| --- | --- |
| Example 72 - ambient temperature conditions | 5876 |
| Example 72- warm temperature conditions | 5176 |
| Example 73 - ambient temperature conditions | 5290 |
| Example 73 - warm temperature conditions | 4987 |
| SR Brand 1 - ambient temperature conditions | 5449 |
| SR Brand 1 - warm temperature conditions | 5554 |

TABLE 12-continued

| Laundry Detergent Composition | Cleaning Value |
| --- | --- |
| SR Brand 2 - ambient temperature conditions | 5491 |
| SR Brand 2 - warm temperature conditions | 4845 |
| SR Brand 3 - ambient temperature conditions | 6175 |
| SR Brand 3 - warm temperature conditions | 5118 |
| SR Brand 4 - ambient temperature conditions | 5521 |
| SR Brand 4 - warm temperature conditions | 5400 |

As is illustrated by the above table, laundry detergents of the present invention produced cleaning results that were comparable to or better than the cleaning results of the brand name stain removers examined at both ambient and warm water temperature conditions.

In Table 13, the cleaning ability of the exemplary embodiment Example 74 was compared to four brand name stain removers: (1) SR Brand 1; (2) SR Brand 2; (3) SR Brand 3; and (4) SR Brand 4. In this study, both ambient and warm water temperature conditions were used. Additionally, all ten stains were examined.

TABLE 13

| Laundry Detergent Composition | Cleaning Value |
| --- | --- |
| Example 74 - ambient temperature conditions | 6133 |
| Example 74 - warm temperature conditions | 7242 |
| SR Brand 1 - ambient temperature conditions | 5779 |
| SR Brand 1 - warm temperature conditions | 7115 |
| SR Brand 2 - ambient temperature conditions | 5762 |
| SR Brand 2 - warm temperature conditions | 5814 |
| SR Brand 3 - ambient temperature conditions | 6921 |
| SR Brand 3 - warm temperature conditions | 6506 |
| SR Brand 4 - ambient temperature conditions | 5828 |
| SR Brand 4 - warm temperature conditions | 5814 |

As is illustrated by the above table, laundry detergents of the present invention produced cleaning results that were comparable to or better than the cleaning results of the brand name stain removers examined at both ambient and warm water temperature conditions.

In Table 14, the cleaning ability of four exemplary embodiments, Example 68, Example 69, Example 70 and Example 83, were compared to two brand name laundry detergents: (1) LD Brand 1; and (2) LD Brand 3. In this study, both ambient and warm water temperature conditions were used. Additionally, all ten stains were examined.

TABLE 14

| Laundry Detergent Composition | Cleaning Value |
| --- | --- |
| Example 68 - ambient temperature conditions | 6543 |
| Example 68 - warm temperature conditions | 6485 |
| Example 69 - ambient temperature conditions | 6161 |
| Example 70 - ambient temperature conditions | 6095 |
| Example 83 - ambient temperature conditions | 5523 |
| LD Brand 1 - ambient temperature conditions | 6453 |
| LD Brand 1 - warm temperature conditions | 6843 |
| LD Brand 3 - ambient temperature conditions | 5543 |
| LD Brand 3 - warm temperature conditions | 5715 |

As is illustrated by the above table, laundry detergents of the present invention produced cleaning results that were comparable to or better than the cleaning results of the brand name laundry detergents examined at both ambient water temperature conditions and warm water temperature conditions.

In Table 15, the cleaning ability of four exemplary embodiments, Example 75, Example 76, Example 77 and Example 78, were compared to four brand name laundry detergents: (1) LD Brand 1; (2) LD Brand 2; (3) LD Brand 3; and (4) LD Brand 4. In this study, both ambient and warm water temperature conditions were used. Additionally, all ten stains were examined.

TABLE 15

| Laundry Detergent Composition | Cleaning Value |
|---|---|
| Example 75 - ambient temperature conditions | 5574 |
| Example 75 - warm temperature conditions | 5203 |
| Example 76 - ambient temperature conditions | 5318 |
| Example 76 - warm temperature conditions | 5016 |
| Example 77 - ambient temperature conditions | 5343 |
| Example 77 - warm temperature conditions | 5767 |
| Example 78 - ambient temperature conditions | 5164 |
| Example 78 - warm temperature conditions | 5288 |
| LD Brand 1 - ambient temperature conditions | 5463 |
| LD Brand 1 - warm temperature conditions | 4835 |
| LD Brand 2 - ambient temperature conditions | 4727 |
| LD Brand 2 - warm temperature conditions | 4477 |
| LD Brand 3 - ambient temperature conditions | 5341 |
| LD Brand 4 - ambient temperature conditions | 5264 |

As is illustrated by the above table, laundry detergents of the present invention produced cleaning results that were comparable to or better than the cleaning results of the brand name laundry detergents examined at both ambient water temperature conditions and warm water temperature conditions.

In Table 16, the cleaning ability of four exemplary embodiments, Example 79, Example 80, Example 81 and Example 82, were compared to one brand name laundry detergent: (1) LD Brand 1. In this study, ambient water temperature conditions were used. Additionally, all ten stains were examined. For this study, in order to minimize any error and to obtain highly accurate cleaning values for the stain after wash, each numerical value (R, G, B) was measured either 2 or 3 separate times and the average for each of the numerical values was used in computing the 30 measurements for the stain after wash. The same methodology as described above was then used to obtain the cleaning value.

TABLE 16

| Laundry Detergent Composition | Cleaning Value |
|---|---|
| Example 79 - ambient temperature conditions | 5218 |
| Example 80 - ambient temperature conditions | 5122 |
| Example 81 - ambient temperature conditions | 5278 |
| Example 82 - ambient temperature conditions | 4831 |
| LD Brand 1 - ambient temperature conditions | 5102 |

As is illustrated by the above table, laundry detergents of the present invention produced cleaning results that were comparable to or better than the cleaning results of the brand name laundry detergent examined at ambient water temperature condition.

In Table 17, the cleaning ability of three exemplary embodiments, Example 84, Example 85 and Example 86, were compared to one brand name laundry detergent: (1) LD Brand 1. In this study, ambient water temperature conditions were used. Additionally, as noted above, nine stains were examined. For this study, in order to minimize any error and to obtain highly accurate cleaning values for both the stains before wash and after wash, each numerical value (R, G, B) was measured 3 separate times (for a total of 81 measurements before wash and 81 measurements after wash) and the average for each of the numerical values was used in computing the 27 measurements (the 3 values for each of R, G, B multiplied by the nine stains) for the stain before wash and for the stain after wash. The same methodology as described above was then used to obtain the cleaning value.

TABLE 17

| Laundry Detergent Composition | Cleaning Value |
|---|---|
| Example 84 - ambient temperature conditions | 4402 |
| Example 85 - ambient temperature conditions | 4273 |
| Example 86 - ambient temperature conditions | 4202 |
| LD Brand 1 - ambient temperature conditions | 4352 |

As is illustrated by the above table, laundry detergents of the present invention produced cleaning results that were comparable to or better than the cleaning results of the brand name laundry detergent examined at ambient water temperature condition.

In Table 18, the cleaning ability of one exemplary embodiment, Example 84, was compared to three brand name laundry detergents: (1) LD Brand 1, (2) LD Brand 3 and (3) LD Brand 4. In this study, ambient water temperature conditions were used. Additionally, as noted above, seven stains were examined. For this study, in order to minimize any error and to obtain highly accurate cleaning values for both the stains before wash and after wash, each numerical value (R, G, B) was measured 3 separate times (for a total of 63 measurements before wash and 63 measurements after wash) and the average for each of the numerical values was used in computing the 21 measurements (the 3 values for each of R, G, B multiplied by the seven stains) for the stain before wash and for the stain after wash. The same methodology as described above was then used to obtain the cleaning value.

TABLE 18

| Laundry Detergent Composition | Cleaning Value |
|---|---|
| Example 84 - ambient temperature conditions | 5952 |
| LD Brand 1 - ambient temperature conditions | 5948 |
| LD Brand 3 - ambient temperature conditions | 5794 |
| LD Brand 4 - ambient temperature conditions | 5766 |

As is illustrated by the above table, laundry detergents of the present invention produced cleaning results that were better than the cleaning results of the brand name laundry detergent examined at ambient water temperature condition.

While various embodiments have been described above, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the methods described above and illustrated in the drawings are shown as a sequence of steps, this was done solely for the sake of illustration. Accordingly, it is contemplated that some steps may be added, some steps may be omitted, the order of steps may be re-arranged, and some steps may be performed in parallel.

What is claimed is:
1. A cleaning composition comprising:
   (a) a fermented fruit solution wherein the total acid content of the fermented fruit solution is greater than or equal to 3.0%, the fermented fruit solution prepared by fermenting a pre-fermented fruit solution with lactic acid bacteria, wherein the pre-fermented fruit solution comprises:
   (i) about 2 to about 20 weight percent of a sugar based on the total weight of the pre-fermented fruit solution,

(ii) about 20 to about 50 weight percent of a fruit puree based on the total weight of the pre-fermented fruit solution, wherein the fruit is more than 90% pineapple, (iii) about 30 to about 75 weight percent of a water based on the total weight of the pre-fermented fruit solution, wherein a brix level of the pre-fermented fruit solution is about 12% to about 24%, (b) an amount of about 2 to about 30 weight percent based on the total weight of the composition of sodium citrate, sodium bicarbonate, boric acid, or a mixture thereof, and (c) a surfactant.

2. The cleaning composition of claim 1, wherein the total weight percent of sodium citrate, sodium bicarbonate, boric acid, or a mixture thereof is about 5 to about 30 weight percent based on the total weight of the composition.

3. The cleaning composition of claim 1, wherein the total weight percent of sodium citrate, sodium bicarbonate, and boric acid, or a mixture thereof is about 10 to about 28 weight percent based on the total weight of the composition.

4. The cleaning composition of claim 2, wherein the total weight percent of sodium citrate, sodium bicarbonate, and boric acid, or a mixture thereof is about 15 to about 27.5 weight percent based on the total weight of the composition.

5. The cleaning composition of claim 1, wherein the composition comprises sodium citrate in an amount of about 5 to about 25 weight percent based on the total weight of the composition and boric acid in an amount of about 0.5 to about 5 weight percent based on the total weight of the composition.

6. The cleaning composition of claim 5, wherein the composition comprises sodium citrate in an amount of about 15 to about 25 weight percent based on the total weight of the composition and boric acid in an amount of about 1 to about 3 weight percent based on the total weight of the composition.

7. The cleaning composition of claim 6, wherein the composition comprises sodium citrate in an amount of about 20 to about 25 weight percent based on the total weight of the composition and boric acid in an amount of about 1.5 to about 2.5 weight percent based on the total weight of the composition.

8. The cleaning composition of claim 1, wherein the composition comprises sodium citrate in an amount of about 5 to about 25 weight percent based on the total weight of the composition.

9. The cleaning composition of claim 8, wherein the composition comprises sodium citrate in an amount of about 10 to about 25 weight percent based on the total weight of the composition.

10. The cleaning composition of claim 9, wherein the composition comprises sodium citrate in an amount of about 15 to about 21 weight percent based on the total weight of the composition.

11. The cleaning composition of claim 1 further comprising:
at least one emulsifier;
at least one thickener;
at least one pH adjusting agent; and
at least one solvent, wherein the solvent is not water.

12. The cleaning composition of claim 11, wherein the at least one emulsifier is present in an amount of about 0.1 to about 2.5 weight percent based on the total weight of the composition.

13. The cleaning composition of claim 11, wherein the emulsifier is glycerol.

14. The cleaning composition of claim 11, wherein the at least one thickener is present in an amount of about 0.1 to about 2 weight percent based on the total weight of the composition.

15. The cleaning composition of claim 11, wherein the at least one thickener is selected from the group consisting of sodium chloride, natural gums including guar gum, xanthan gum and gum arabic, and mixtures thereof.

16. The cleaning composition of claim 11, wherein the at least one pH adjusting agent is present in an amount of about 0.01 to about 2 weight percent based on the total weight of the composition.

17. The cleaning composition of claim 11, wherein the at least one pH adjusting agent is selected from the group consisting of sodium hydroxide, potassium hydroxide and mixtures thereof.

18. The cleaning composition of claim 11, wherein the at least one solvent is present in an amount of about 0.2 to about 2 weight percent based on the total weight of the composition.

19. The cleaning composition of claim 11, wherein the at least one solvent is present in an amount of about 0.5 to about 2 weight percent based on the total weight of the composition.

20. The cleaning composition of claim 11, wherein the at least one solvent is ethanol.

21. The cleaning composition of claim 11, wherein the surfactant is a natural based surfactant.

22. The cleaning composition of claim 21, wherein the natural based surfactant is selected from the group consisting of alkyl polyglycoside, sodium lauryl sulfate, cocamidopropyl betaine and mixtures thereof.

23. The cleaning composition of claim 21, wherein the natural based surfactant is present in an amount of about 1 to about 23 weight percent based on the total weight of the composition.

24. The cleaning composition of claim 23, wherein the natural based surfactant is present in an amount of about 1 to about 15 weight percent based on the total weight of the composition.

25. The cleaning composition of claim 24, wherein the natural based surfactant is present in an amount of about 2 to about 15 weight percent based on the total weight of the composition.

26. The cleaning composition of claim 25, wherein the natural based surfactant is present in an amount of about 5 to about 15 weight percent based on the total weight of the composition.

27. The cleaning composition of claim 21, wherein the natural based surfactant is alkyl polyglycoside and is present in an amount of about 2 to about 8 weight percent based on the total weight of the composition.

28. The cleaning composition of claim 27, wherein the natural based surfactant is alkyl polyglycoside and is present in an amount of about 5 to about 6.5 weight percent based on the total weight of the composition.

29. The cleaning composition of claim 21, wherein the natural based surfactant is sodium lauryl sulfate and is present in an amount of about 5 to about 15 weight percent based on the total weight of the composition.

30. The cleaning composition of claim 29, wherein the natural based surfactant is sodium lauryl sulfate and is present in an amount of about 8 to about 15 weight percent based on the total weight of the composition.

31. The cleaning composition of claim 1 further comprising:
 at least one corrosion inhibitor.

32. The cleaning composition of claim 31, wherein the at least one corrosion inhibitor is present in an amount of about 0.1 to about 2.5 weight percent based on the total weight of the composition.

33. The cleaning composition of claim 31, wherein the at least one corrosion inhibitor is selected from the group consisting of gum arabic, sodium polyaspartate and mixtures thereof.

34. The cleaning composition of claim 1 further comprising:
 a preservative.

35. The cleaning composition of claim 34, wherein the preservative is selected from the group consisting of benzoic acid, potassium sorbate, nisin, natamycin and mixtures thereof.

36. The cleaning composition of claim 35, wherein the preservative is selected from the group consisting of potassium sorbate, nisin, natamycin and mixtures thereof.

37. The cleaning composition of claim 34, wherein the preservative is present in an amount not greater than about 1 weight percent based on the total weight of the composition.

38. The cleaning composition of claim 1 further comprising:
 an essential oil.

\* \* \* \* \*